(12) United States Patent
Petzelbauer

(10) Patent No.: US 7,494,973 B2
(45) Date of Patent: *Feb. 24, 2009

(54) THERAPEUTIC FIBRIN-DERIVED PEPTIDES AND USES THEREOF

(75) Inventor: Peter Petzelbauer, Vienna (AT)

(73) Assignee: Fibrex Medical Research & Development GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 11/542,050

(22) Filed: Oct. 3, 2006

(65) Prior Publication Data

US 2007/0037749 A1    Feb. 15, 2007

Related U.S. Application Data

(63) Continuation of application No. 10/459,030, filed on Jun. 11, 2003, now Pat. No. 7,271,144, which is a continuation of application No. PCT/AT01/00387, filed on Dec. 7, 2001.

(30) Foreign Application Priority Data

Dec. 12, 2000    (AU)    ............... A 2063/2000

(51) Int. Cl.
  *A61K 38/00*    (2006.01)
(52) U.S. Cl. ........................................ 514/2
(58) Field of Classification Search ............. None
  See application file for complete search history.

(56) References Cited

U.S. PATENT DOCUMENTS

| 4,927,916 A | 5/1990 | Matsueda et al. | |
| 5,720,934 A * | 2/1998 | Dean et al. | 424/1.69 |
| 2003/0078613 A1 | 4/2003 | Heidner | |

FOREIGN PATENT DOCUMENTS

| DE | 19729591 | 2/1999 |
| WO | WO/93/21962 | 11/1993 |
| WO | WO/02/48180 | 6/2002 |

OTHER PUBLICATIONS

Everse, S. J. (1999). Conformational Changes in Fragments D and Double-D from Human Fibrin(ogen) Upon Binding the Peptide Ligand Gly-His-Arg-Pro-Amide. Biochemistry, Bd. 38, 18: 2941-2946.
Gröger et al. (1999). J. Immunol. Method, 222: 101-109.
Herrick, S. et al. (1999). Fibrinogen, International Journal of Biochemistry and Cell Biology, Bd. 31: 741-746.
Petzelbauer et al. (1996). J. Invest. Dermatol., 1996, 107: 576-581.
Kawasaki, K. (1989). Amino Acids and Peptides XII: Synthetic Peptides Related to the N-Terminal Portion of Fibrin Alpha-chain and their Inhibitory Effects on Fibrinogen/ Thrombin Clotting. Thrombosis Research, Bd. 56: 757-762.
Skogen, W. F. et al. (1988). Blood 71: 1475-1479.
Henschen et al. (1985). High Performance Liquid Chromatography VCH.
Engelhart et al. (1984). Chromatography, 19: 77.
Ikematsu. (1984). Radioimmunoassay of Fibrinopeptide, Bd. 28, Nr. 1, 20-24, Table 2.
Harenberg, J. (1983). Biodistribution of Human Fibrinogen-derived Peptides in Rabbits. Fibrinogen: Struct. Variants Interact., 271-278.
Nieuwenhuizen et al. (1983). Biochem Biophys Acta, entitled Plasminogen activation by tissue activator is accelerated in the presence of fibrin(ogen) cyanogen bromide fragment FCB-2, 755: 531-533.
Carpino et al. (1981). J. Amer. Chem. Soc., 37: 3404-3409.
Blomback et al. (1968). Nature, entitled N-Terminal Disulphide Knot Of Human Fibrinogen, 218: 130-134.
Merrifield, R. B. (1963). J. Amer. Chem. Soc., 85: 2149-2154.

* cited by examiner

*Primary Examiner*—Robert B. Mondesi
(74) *Attorney, Agent, or Firm*—Baker Botts L.L.P.

(57) ABSTRACT

The invention relates to peptides having the general formula (I), or a salt or amide thereof, wherein $R_1$ and $R_2$ are either the same or different, wherein $R_1$ and $R_2$ are each selected from the group consisting of hydrogen and a saturated or unsaturated hydrocarbon residue, said residue having from 1 to 10 carbon atoms, wherein $Z_1$ is selected from the group consisting of histidine and proline, wherein $Z_2$ is selected from the group consisting of an arginine and a peptide comprising an initial arginine and having from 2 to 30 amino acids. The invention also relates to methods using the peptides of the present invention in the treatment of inflammation.

3 Claims, No Drawings

SEQUENCE LISTING

<160> NUMBER OF SEQ ID NOS: 296

<210> SEQ ID NO 1
<211> LENGTH: 3
<212> TYPE: PRT
<213> ORGANISM: Artificial Sequence
<220> FEATURE:
<223> OTHER INFORMATION: peptide of formula I

```
<400> SEQUENCE: 1

Gly His Arg
 1

<210> SEQ ID NO 2
<211> LENGTH: 3
<212> TYPE: PRT
<213> ORGANISM: Artificial Sequence
<220> FEATURE:
<223> OTHER INFORMATION: peptide of formula I

<400> SEQUENCE: 2

Gly Pro Arg
 1

<210> SEQ ID NO 3
<211> LENGTH: 4
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: 4
<223> OTHER INFORMATION: Xaa=any amino acid

<400> SEQUENCE: 3

Gly His Arg Xaa
 1

<210> SEQ ID NO 4
<211> LENGTH: 4
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: 4
<223> OTHER INFORMATION: Xaa=any amino acid

<400> SEQUENCE: 4

Gly Pro Arg Xaa
 1

<210> SEQ ID NO 5
<211> LENGTH: 5
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(5)
<223> OTHER INFORMATION: Xaa=any amino acid

<400> SEQUENCE: 5

Gly His Arg Xaa Xaa
 1               5

<210> SEQ ID NO 6
<211> LENGTH: 5
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
```

```
<222> LOCATION: (4)...(5)
<223> OTHER INFORMATION: Xaa=any amino acid

<400> SEQUENCE: 6

Gly Pro Arg Xaa Xaa
 1               5

<210> SEQ ID NO 7
<211> LENGTH: 6
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(6)
<223> OTHER INFORMATION: Xaa=any amino acid

<400> SEQUENCE: 7

Gly His Arg Xaa Xaa Xaa
 1               5

<210> SEQ ID NO 8
<211> LENGTH: 6
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(6)
<223> OTHER INFORMATION: Xaa=any amino acid

<400> SEQUENCE: 8

Gly Pro Arg Xaa Xaa Xaa
 1               5

<210> SEQ ID NO 9
<211> LENGTH: 7
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(7)
<223> OTHER INFORMATION: Xaa=any amino acid

<400> SEQUENCE: 9

Gly His Arg Xaa Xaa Xaa Xaa
 1               5

<210> SEQ ID NO 10
<211> LENGTH: 7
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(7)
<223> OTHER INFORMATION: Xaa=any amino acid

<400> SEQUENCE: 10

Gly Pro Arg Xaa Xaa Xaa Xaa
 1               5

<210> SEQ ID NO 11
<211> LENGTH: 8
```

```
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(8)
<223> OTHER INFORMATION: Xaa=any amino acid

<400> SEQUENCE: 11

Gly His Arg Xaa Xaa Xaa Xaa Xaa
 1               5

<210> SEQ ID NO 12
<211> LENGTH: 8
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(8)
<223> OTHER INFORMATION: Xaa=any amino acid

<400> SEQUENCE: 12

Gly Pro Arg Xaa Xaa Xaa Xaa Xaa
 1               5

<210> SEQ ID NO 13
<211> LENGTH: 9
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(9)
<223> OTHER INFORMATION: Xaa=any amino acid

<400> SEQUENCE: 13

Gly His Arg Xaa Xaa Xaa Xaa Xaa Xaa
 1               5

<210> SEQ ID NO 14
<211> LENGTH: 9
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(9)
<223> OTHER INFORMATION: Xaa=any amino acid

<400> SEQUENCE: 14

Gly Pro Arg Xaa Xaa Xaa Xaa Xaa Xaa
 1               5

<210> SEQ ID NO 15
<211> LENGTH: 10
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(10)
<223> OTHER INFORMATION: Xaa=any amino acid

<400> SEQUENCE: 15
```

```
Gly His Arg Xaa Xaa Xaa Xaa Xaa Xaa Xaa
1               5                   10

<210> SEQ ID NO 16
<211> LENGTH: 10
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(10)
<223> OTHER INFORMATION: Xaa=any amino acid

<400> SEQUENCE: 16

Gly Pro Arg Xaa Xaa Xaa Xaa Xaa Xaa Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(11)
<223> OTHER INFORMATION: Xaa=any amino acid

<400> SEQUENCE: 17

Gly His Arg Xaa Xaa Xaa Xaa Xaa Xaa Xaa Xaa
1               5                   10

<210> SEQ ID NO 18
<211> LENGTH: 11
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(11)
<223> OTHER INFORMATION: Xaa=any amino acid

<400> SEQUENCE: 18

Gly Pro Arg Xaa Xaa Xaa Xaa Xaa Xaa Xaa Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(12)
<223> OTHER INFORMATION: Xaa=any amino acid

<400> SEQUENCE: 19

Gly His Arg Xaa Xaa Xaa Xaa Xaa Xaa Xaa Xaa Xaa
1               5                   10

<210> SEQ ID NO 20
<211> LENGTH: 12
<212> TYPE: PRT
<213> ORGANISM: Artificial Sequence
<220> FEATURE:
<223> OTHER INFORMATION: peptide of formula I
<220> FEATURE:
```

```
<221> NAME/KEY: VARIANT
<222> LOCATION: (4)...(12)
<223> OTHER INFORMATION: Xaa=any amino acid

<400> SEQUENCE: 20

Gly Pro Arg Xaa Xaa Xaa Xaa Xaa Xaa Xaa Xaa
 1               5                  10

<210> SEQ ID NO 21
<211> LENGTH: 13
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(13)
<223> OTHER INFORMATION: Xaa=any amino acid

<400> SEQUENCE: 21

Gly His Arg Xaa Xaa Xaa Xaa Xaa Xaa Xaa Xaa Xaa
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(13)
<223> OTHER INFORMATION: Xaa=any amino acid

<400> SEQUENCE: 22

Gly Pro Arg Xaa Xaa Xaa Xaa Xaa Xaa Xaa Xaa Xaa
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(14)
<223> OTHER INFORMATION: Xaa=any amino acid

<400> SEQUENCE: 23

Gly His Arg Xaa Xaa Xaa Xaa Xaa Xaa Xaa Xaa Xaa Xaa
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(14)
<223> OTHER INFORMATION: Xaa=any amino acid

<400> SEQUENCE: 24

Gly Pro Arg Xaa Xaa Xaa Xaa Xaa Xaa Xaa Xaa Xaa Xaa
 1               5                  10

<210> SEQ ID NO 25
```

```
<211> LENGTH: 15
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(15)
<223> OTHER INFORMATION: Xaa=any amino acid

<400> SEQUENCE: 25

Gly His Arg Xaa Xaa Xaa Xaa Xaa Xaa Xaa Xaa Xaa Xaa Xaa Xaa
 1               5                  10                  15

<210> SEQ ID NO 26
<211> LENGTH: 15
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(15)
<223> OTHER INFORMATION: Xaa=any amino acid

<400> SEQUENCE: 26

Gly Pro Arg Xaa Xaa Xaa Xaa Xaa Xaa Xaa Xaa Xaa Xaa Xaa Xaa
 1               5                  10                  15

<210> SEQ ID NO 27
<211> LENGTH: 16
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(16)
<223> OTHER INFORMATION: Xaa=any amino acid

<400> SEQUENCE: 27

Gly His Arg Xaa Xaa Xaa Xaa Xaa Xaa Xaa Xaa Xaa Xaa Xaa Xaa Xaa
 1               5                  10                  15

<210> SEQ ID NO 28
<211> LENGTH: 16
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(16)
<223> OTHER INFORMATION: Xaa=any amino acid

<400> SEQUENCE: 28

Gly Pro Arg Xaa Xaa Xaa Xaa Xaa Xaa Xaa Xaa Xaa Xaa Xaa Xaa Xaa
 1               5                  10                  15

<210> SEQ ID NO 29
<211> LENGTH: 17
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(17)
<223> OTHER INFORMATION: Xaa=any amino acid

<400> SEQUENCE: 29
```

Gly His Arg Xaa Xaa Xaa Xaa Xaa Xaa Xaa Xaa Xaa Xaa Xaa Xaa
1               5                   10                  15

Xaa

<210> SEQ ID NO 30
<211> LENGTH: 17
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(17)
<223> OTHER INFORMATION: Xaa=any amino acid

<400> SEQUENCE: 30

Gly Pro Arg Xaa Xaa Xaa Xaa Xaa Xaa Xaa Xaa Xaa Xaa Xaa Xaa
1               5                   10                  15

Xaa

<210> SEQ ID NO 31
<211> LENGTH: 18
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(18)
<223> OTHER INFORMATION: Xaa=any amino acid

<400> SEQUENCE: 31

Gly His Arg Xaa Xaa Xaa Xaa Xaa Xaa Xaa Xaa Xaa Xaa Xaa Xaa
1               5                   10                  15

Xaa Xaa

<210> SEQ ID NO 32
<211> LENGTH: 18
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(18)
<223> OTHER INFORMATION: Xaa=any amino acid

<400> SEQUENCE: 32

Gly Pro Arg Xaa Xaa Xaa Xaa Xaa Xaa Xaa Xaa Xaa Xaa Xaa Xaa
1               5                   10                  15

Xaa Xaa

<210> SEQ ID NO 33
<211> LENGTH: 20
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(20)
<223> OTHER INFORMATION: Xaa=any amino acid

<400> SEQUENCE: 33

Gly His Arg Xaa Xaa Xaa Xaa Xaa Xaa Xaa Xaa Xaa Xaa Xaa Xaa
1               5                   10                  15

```
Xaa Xaa Xaa Xaa
         20

<210> SEQ ID NO 34
<211> LENGTH: 20
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(20)
<223> OTHER INFORMATION: Xaa=any amino acid

<400> SEQUENCE: 34

Gly Pro Arg Xaa Xaa Xaa Xaa Xaa Xaa Xaa Xaa Xaa Xaa Xaa Xaa
 1               5                  10                  15

Xaa Xaa Xaa Xaa
         20

<210> SEQ ID NO 35
<211> LENGTH: 21
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(21)
<223> OTHER INFORMATION: Xaa=any amino acid

<400> SEQUENCE: 35

Gly His Arg Xaa Xaa Xaa Xaa Xaa Xaa Xaa Xaa Xaa Xaa Xaa Xaa
 1               5                  10                  15

Xaa Xaa Xaa Xaa Xaa
         20

<210> SEQ ID NO 36
<211> LENGTH: 21
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(21)
<223> OTHER INFORMATION: Xaa=any amino acid

<400> SEQUENCE: 36

Gly Pro Arg Xaa Xaa Xaa Xaa Xaa Xaa Xaa Xaa Xaa Xaa Xaa Xaa
 1               5                  10                  15

Xaa Xaa Xaa Xaa Xaa
         20

<210> SEQ ID NO 37
<211> LENGTH: 22
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(22)
<223> OTHER INFORMATION: Xaa=any amino acid

<400> SEQUENCE: 37

Gly His Arg Xaa Xaa Xaa Xaa Xaa Xaa Xaa Xaa Xaa Xaa Xaa Xaa
```

```
                1               5                  10                 15

Xaa Xaa Xaa Xaa Xaa Xaa
                20

<210> SEQ ID NO 38
<211> LENGTH: 22
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(22)
<223> OTHER INFORMATION: Xaa=any amino acid

<400> SEQUENCE: 38

Gly Pro Arg Xaa Xaa Xaa Xaa Xaa Xaa Xaa Xaa Xaa Xaa Xaa Xaa
  1               5                  10                 15

Xaa Xaa Xaa Xaa Xaa Xaa
                20

<210> SEQ ID NO 39
<211> LENGTH: 23
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(23)
<223> OTHER INFORMATION: Xaa=any amino acid

<400> SEQUENCE: 39

Gly His Arg Xaa Xaa Xaa Xaa Xaa Xaa Xaa Xaa Xaa Xaa Xaa Xaa
  1               5                  10                 15

Xaa Xaa Xaa Xaa Xaa Xaa Xaa
                20

<210> SEQ ID NO 40
<211> LENGTH: 23
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(23)
<223> OTHER INFORMATION: Xaa=any amino acid

<400> SEQUENCE: 40

Gly Pro Arg Xaa Xaa Xaa Xaa Xaa Xaa Xaa Xaa Xaa Xaa Xaa Xaa
  1               5                  10                 15

Xaa Xaa Xaa Xaa Xaa Xaa Xaa
                20

<210> SEQ ID NO 41
<211> LENGTH: 24
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(24)
<223> OTHER INFORMATION: Xaa=any amino acid

<400> SEQUENCE: 41
```

```
Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 42
<211> LENGTH: 24
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(24)
<223> OTHER INFORMATION: Xaa=any amino acid

<400> SEQUENCE: 42

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 43
<211> LENGTH: 25
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(25)
<223> OTHER INFORMATION: Xaa=any amino acid

<400> SEQUENCE: 43

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 44
<211> LENGTH: 25
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(25)
<223> OTHER INFORMATION: Xaa=any amino acid

<400> SEQUENCE: 44

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 45
<211> LENGTH: 26
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(26)
<223> OTHER INFORMATION: Xaa=any amino acid

<400> SEQUENCE: 45
```

-continued

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 46
<211> LENGTH: 26
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(26)
<223> OTHER INFORMATION: Xaa=any amino acid

<400> SEQUENCE: 46

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 47
<211> LENGTH: 27
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(27)
<223> OTHER INFORMATION: Xaa=any amino acid

<400> SEQUENCE: 47

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 48
<211> LENGTH: 27
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(27)
<223> OTHER INFORMATION: Xaa=any amino acid

<400> SEQUENCE: 48

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 49
<211> LENGTH: 28
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(28)
<223> OTHER INFORMATION: Xaa=any amino acid

```
<400> SEQUENCE: 49

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 50
<211> LENGTH: 28
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(28)
<223> OTHER INFORMATION: peptide of formula I Xaa=any Xaa=any amino acid

<400> SEQUENCE: 50

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 51
<211> LENGTH: 29
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(29)
<223> OTHER INFORMATION: Xaa=any amino acid

<400> SEQUENCE: 51

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 52
<211> LENGTH: 29
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(29)
<223> OTHER INFORMATION: Xaa=any amino acid

<400> SEQUENCE: 52

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 53
<211> LENGTH: 30
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(30)
<223> OTHER INFORMATION: Xaa=any amino acid
```

-continued

<400> SEQUENCE: 53

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 54
<211> LENGTH: 30
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(30)
<223> OTHER INFORMATION: Xaa=any amino acid

<400> SEQUENCE: 54

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(31)
<223> OTHER INFORMATION: Xaa=any amino acid

<400> SEQUENCE: 55

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(31)
<223> OTHER INFORMATION: Xaa=any amino acid

<400> SEQUENCE: 56

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(32)

<223> OTHER INFORMATION: Xaa=any amino acid

<400> SEQUENCE: 57

Gly His Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(32)
<223> OTHER INFORMATION: Xaa=any amino acid

<400> SEQUENCE: 58

Gly Pro Arg Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 59
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 59

Gly His Arg Pro Leu Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 60

Gly Pro Arg Pro Leu Xaa Xaa
1               5

<210> SEQ ID NO 61
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 61

Gly His Arg Val Leu Xaa Xaa

```
<210> SEQ ID NO 62
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 62

Gly Pro Arg Val Leu Xaa Xaa
 1               5

<210> SEQ ID NO 63
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 63

Gly His Arg Pro Val Xaa Xaa
 1               5

<210> SEQ ID NO 64
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 64

Gly Pro Arg Pro Val Xaa Xaa
 1               5

<210> SEQ ID NO 65
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(7)
<223> OTHER INFORMATION: Xaa=any amino acid

<400> SEQUENCE: 65

Gly His Arg Val Val Xaa Xaa
 1               5

<210> SEQ ID NO 66
<211> LENGTH: 7
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
```

```
<222> LOCATION: (6)...(7)
<223> OTHER INFORMATION: Xaa=any amino acid

<400> SEQUENCE: 66

Gly Pro Arg Val Val Xaa Xaa
 1               5

<210> SEQ ID NO 67
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 67

Gly His Arg Pro Leu Xaa Xaa Xaa
 1               5

<210> SEQ ID NO 68
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 68

Gly Pro Arg Pro Leu Xaa Xaa Xaa
 1               5

<210> SEQ ID NO 69
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 69

Gly His Arg Val Leu Xaa Xaa Xaa
 1               5

<210> SEQ ID NO 70
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 70

Gly Pro Arg Val Leu Xaa Xaa Xaa
 1               5

<210> SEQ ID NO 71
<211> LENGTH: 8
```

```
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 71

Gly His Arg Pro Val Xaa Xaa Xaa
 1               5

<210> SEQ ID NO 72
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 72

Gly Pro Arg Pro Val Xaa Xaa Xaa
 1               5

<210> SEQ ID NO 73
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 73

Gly His Arg Val Val Xaa Xaa Xaa
 1               5

<210> SEQ ID NO 74
<211> LENGTH: 8
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(8)
<223> OTHER INFORMATION: Xaa=any amino acid

<400> SEQUENCE: 74

Gly Pro Arg Val Val Xaa Xaa Xaa
 1               5

<210> SEQ ID NO 75
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 75
```

```
Gly His Arg Pro Leu Xaa Xaa Xaa Xaa
 1               5

<210> SEQ ID NO 76
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 76

Gly Pro Arg Pro Leu Xaa Xaa Xaa Xaa
 1               5

<210> SEQ ID NO 77
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 77

Gly His Arg Val Leu Xaa Xaa Xaa Xaa
 1               5

<210> SEQ ID NO 78
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 78

Gly Pro Arg Val Leu Xaa Xaa Xaa Xaa
 1               5

<210> SEQ ID NO 79
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 79

Gly His Arg Pro Val Xaa Xaa Xaa Xaa
 1               5

<210> SEQ ID NO 80
<211> LENGTH: 9
<212> TYPE: PRT
<213> ORGANISM: Artificial Sequence
<220> FEATURE:
<223> OTHER INFORMATION: peptide of formula II
<220> FEATURE:
```

```
<221> NAME/KEY: VARIANT
<222> LOCATION: (6)...(9)
<223> OTHER INFORMATION: Xaa=any amino acid

<400> SEQUENCE: 80

Gly Pro Arg Pro Val Xaa Xaa Xaa Xaa
 1               5

<210> SEQ ID NO 81
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 81

Gly His Arg Val Val Xaa Xaa Xaa Xaa
 1               5

<210> SEQ ID NO 82
<211> LENGTH: 9
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(9)
<223> OTHER INFORMATION: Xaa=any amino acid

<400> SEQUENCE: 82

Gly Pro Arg Val Val Xaa Xaa Xaa Xaa
 1               5

<210> SEQ ID NO 83
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 83

Gly His Arg Pro Leu Xaa Xaa Xaa Xaa Xaa
 1               5                  10

<210> SEQ ID NO 84
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 84

Gly Pro Arg Pro Leu Xaa Xaa Xaa Xaa Xaa
 1               5                  10

<210> SEQ ID NO 85
```

-continued

```
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 85

Gly His Arg Val Leu Xaa Xaa Xaa Xaa Xaa
 1               5                  10

<210> SEQ ID NO 86
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 86

Gly Pro Arg Val Leu Xaa Xaa Xaa Xaa Xaa
 1               5                  10

<210> SEQ ID NO 87
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 87

Gly His Arg Pro Val Xaa Xaa Xaa Xaa Xaa
 1               5                  10

<210> SEQ ID NO 88
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 88

Gly Pro Arg Pro Val Xaa Xaa Xaa Xaa Xaa
 1               5                  10

<210> SEQ ID NO 89
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 89
```

```
Gly His Arg Val Val Xaa Xaa Xaa Xaa Xaa
1               5                   10
```

<210> SEQ ID NO 90
<211> LENGTH: 10
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(10)
<223> OTHER INFORMATION: Xaa=any amino acid

<400> SEQUENCE: 90

```
Gly Pro Arg Val Val Xaa Xaa Xaa Xaa Xaa
1               5                   10
```

<210> SEQ ID NO 91
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 91

```
Gly His Arg Pro Leu Xaa Xaa Xaa Xaa Xaa Xaa
1               5                   10
```

<210> SEQ ID NO 92
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 92

```
Gly Pro Arg Pro Leu Xaa Xaa Xaa Xaa Xaa Xaa
1               5                   10
```

<210> SEQ ID NO 93
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 93

```
Gly His Arg Val Leu Xaa Xaa Xaa Xaa Xaa Xaa
1               5                   10
```

<210> SEQ ID NO 94
<211> LENGTH: 11
<212> TYPE: PRT
<213> ORGANISM: Artificial Sequence
<220> FEATURE:
<223> OTHER INFORMATION: peptide of formula II

```
<220> FEATURE:
<221> NAME/KEY: VARIANT
<222> LOCATION: (6)...(11)
<223> OTHER INFORMATION: Xaa=any amino acid

<400> SEQUENCE: 94

Gly Pro Arg Val Leu Xaa Xaa Xaa Xaa Xaa Xaa
1               5                   10

<210> SEQ ID NO 95
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 95

Gly His Arg Pro Val Xaa Xaa Xaa Xaa Xaa Xaa
1               5                   10

<210> SEQ ID NO 96
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 96

Gly Pro Arg Pro Val Xaa Xaa Xaa Xaa Xaa Xaa
1               5                   10

<210> SEQ ID NO 97
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 97

Gly His Arg Val Val Xaa Xaa Xaa Xaa Xaa Xaa
1               5                   10

<210> SEQ ID NO 98
<211> LENGTH: 11
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(11)
<223> OTHER INFORMATION: Xaa=any amino acid

<400> SEQUENCE: 98

Gly Pro Arg Val Val Xaa Xaa Xaa Xaa Xaa Xaa
1               5                   10
```

```
<210> SEQ ID NO 99
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 99

Gly His Arg Pro Leu Xaa Xaa Xaa Xaa Xaa Xaa Xaa
 1               5                  10

<210> SEQ ID NO 100
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 100

Gly Pro Arg Pro Leu Xaa Xaa Xaa Xaa Xaa Xaa Xaa
 1               5                  10

<210> SEQ ID NO 101
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 101

Gly His Arg Val Leu Xaa Xaa Xaa Xaa Xaa Xaa Xaa
 1               5                  10

<210> SEQ ID NO 102
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 102

Gly Pro Arg Val Leu Xaa Xaa Xaa Xaa Xaa Xaa Xaa
 1               5                  10

<210> SEQ ID NO 103
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid
```

```
<400> SEQUENCE: 103

Gly His Arg Pro Val Xaa Xaa Xaa Xaa Xaa Xaa Xaa
1               5                   10

<210> SEQ ID NO 104
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 104

Gly Pro Arg Pro Val Xaa Xaa Xaa Xaa Xaa Xaa Xaa
1               5                   10

<210> SEQ ID NO 105
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 105

Gly His Arg Val Val Xaa Xaa Xaa Xaa Xaa Xaa Xaa
1               5                   10

<210> SEQ ID NO 106
<211> LENGTH: 12
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(12)
<223> OTHER INFORMATION: Xaa=any amino acid

<400> SEQUENCE: 106

Gly Pro Arg Val Val Xaa Xaa Xaa Xaa Xaa Xaa Xaa
1               5                   10

<210> SEQ ID NO 107
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 107

Gly His Arg Pro Leu Xaa Xaa Xaa Xaa Xaa Xaa Xaa Xaa
1               5                   10

<210> SEQ ID NO 108
<211> LENGTH: 13
<212> TYPE: PRT
<213> ORGANISM: Artificial Sequence
<220> FEATURE:
```

```
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 108

Gly Pro Arg Pro Leu Xaa Xaa Xaa Xaa Xaa Xaa Xaa Xaa
 1               5                  10

<210> SEQ ID NO 109
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 109

Gly His Arg Val Leu Xaa Xaa Xaa Xaa Xaa Xaa Xaa Xaa
 1               5                  10

<210> SEQ ID NO 110
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 110

Gly Pro Arg Val Leu Xaa Xaa Xaa Xaa Xaa Xaa Xaa Xaa
 1               5                  10

<210> SEQ ID NO 111
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 111

Gly His Arg Pro Val Xaa Xaa Xaa Xaa Xaa Xaa Xaa Xaa
 1               5                  10

<210> SEQ ID NO 112
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 112

Gly Pro Arg Pro Val Xaa Xaa Xaa Xaa Xaa Xaa Xaa Xaa
 1               5                  10
```

```
<210> SEQ ID NO 113
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 113

Gly His Arg Val Val Xaa Xaa Xaa Xaa Xaa Xaa Xaa Xaa
 1               5                  10

<210> SEQ ID NO 114
<211> LENGTH: 13
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(13)
<223> OTHER INFORMATION: Xaa=any amino acid

<400> SEQUENCE: 114

Gly Pro Arg Val Val Xaa Xaa Xaa Xaa Xaa Xaa Xaa Xaa
 1               5                  10

<210> SEQ ID NO 115
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 115

Gly His Arg Pro Leu Xaa Xaa Xaa Xaa Xaa Xaa Xaa Xaa Xaa
 1               5                  10

<210> SEQ ID NO 116
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 116

Gly Pro Arg Pro Leu Xaa Xaa Xaa Xaa Xaa Xaa Xaa Xaa Xaa
 1               5                  10

<210> SEQ ID NO 117
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid
```

```
<400> SEQUENCE: 117

Gly His Arg Val Leu Xaa Xaa Xaa Xaa Xaa Xaa Xaa Xaa Xaa
1               5                   10

<210> SEQ ID NO 118
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 118

Gly Pro Arg Val Leu Xaa Xaa Xaa Xaa Xaa Xaa Xaa Xaa Xaa
1               5                   10

<210> SEQ ID NO 119
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 119

Gly His Arg Pro Val Xaa Xaa Xaa Xaa Xaa Xaa Xaa Xaa Xaa
1               5                   10

<210> SEQ ID NO 120
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 120

Gly Pro Arg Pro Val Xaa Xaa Xaa Xaa Xaa Xaa Xaa Xaa Xaa
1               5                   10

<210> SEQ ID NO 121
<211> LENGTH: 14
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 121

Gly His Arg Val Val Xaa Xaa Xaa Xaa Xaa Xaa Xaa Xaa Xaa
1               5                   10

<210> SEQ ID NO 122
<211> LENGTH: 14
<212> TYPE: PRT
<213> ORGANISM: Artificial Sequence
```

```
<220> FEATURE:
<223> OTHER INFORMATION: peptide of formula II
<220> FEATURE:
<221> NAME/KEY: VARIANT
<222> LOCATION: (6)...(14)
<223> OTHER INFORMATION: Xaa=any amino acid

<400> SEQUENCE: 122

Gly Pro Arg Val Val Xaa Xaa Xaa Xaa Xaa Xaa Xaa Xaa Xaa
 1               5                  10

<210> SEQ ID NO 123
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 123

Gly His Arg Pro Leu Xaa Xaa Xaa Xaa Xaa Xaa Xaa Xaa Xaa Xaa
 1               5                  10                  15

<210> SEQ ID NO 124
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 124

Gly Pro Arg Pro Leu Xaa Xaa Xaa Xaa Xaa Xaa Xaa Xaa Xaa Xaa
 1               5                  10                  15

<210> SEQ ID NO 125
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 125

Gly His Arg Val Leu Xaa Xaa Xaa Xaa Xaa Xaa Xaa Xaa Xaa Xaa
 1               5                  10                  15

<210> SEQ ID NO 126
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 126

Gly Pro Arg Val Leu Xaa Xaa Xaa Xaa Xaa Xaa Xaa Xaa Xaa Xaa
 1               5                  10                  15
```

<210> SEQ ID NO 127
<211> LENGTH: 15
<212> TYPE: PRT
<213> ORGANISM: Artificial Sequence
<220> FEATURE:
<223> OTHER INFORMATION: Xaa=any amino acid
<220> FEATURE:
<221> NAME/KEY: VARIANT
<222> LOCATION: (6)...(15)
<223> OTHER INFORMATION: peptide of formula II

<400> SEQUENCE: 127

Gly His Arg Pro Val Xaa Xaa Xaa Xaa Xaa Xaa Xaa Xaa Xaa Xaa
 1               5                  10                  15

<210> SEQ ID NO 128
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 128

Gly Pro Arg Pro Val Xaa Xaa Xaa Xaa Xaa Xaa Xaa Xaa Xaa Xaa
 1               5                  10                  15

<210> SEQ ID NO 129
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 129

Gly His Arg Val Val Xaa Xaa Xaa Xaa Xaa Xaa Xaa Xaa Xaa Xaa
 1               5                  10                  15

<210> SEQ ID NO 130
<211> LENGTH: 15
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(15)
<223> OTHER INFORMATION: Xaa=any amino acid

<400> SEQUENCE: 130

Gly Pro Arg Val Val Xaa Xaa Xaa Xaa Xaa Xaa Xaa Xaa Xaa Xaa
 1               5                  10                  15

<210> SEQ ID NO 131
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)

<223> OTHER INFORMATION: Xaa=any amino acid

<400> SEQUENCE: 131

Gly His Arg Pro Leu Xaa Xaa Xaa Xaa Xaa Xaa Xaa Xaa Xaa Xaa
 1               5                  10                  15

<210> SEQ ID NO 132
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 132

Gly Pro Arg Pro Leu Xaa Xaa Xaa Xaa Xaa Xaa Xaa Xaa Xaa Xaa
 1               5                  10                  15

<210> SEQ ID NO 133
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 133

Gly His Arg Val Leu Xaa Xaa Xaa Xaa Xaa Xaa Xaa Xaa Xaa Xaa
 1               5                  10                  15

<210> SEQ ID NO 134
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 134

Gly Pro Arg Val Leu Xaa Xaa Xaa Xaa Xaa Xaa Xaa Xaa Xaa Xaa
 1               5                  10                  15

<210> SEQ ID NO 135
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 135

Gly His Arg Pro Val Xaa Xaa Xaa Xaa Xaa Xaa Xaa Xaa Xaa Xaa
 1               5                  10                  15

<210> SEQ ID NO 136
<211> LENGTH: 16
<212> TYPE: PRT

<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 136

Gly Pro Arg Pro Val Xaa Xaa Xaa Xaa Xaa Xaa Xaa Xaa Xaa Xaa
 1               5                  10                  15

<210> SEQ ID NO 137
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 137

Gly His Arg Val Val Xaa Xaa Xaa Xaa Xaa Xaa Xaa Xaa Xaa Xaa
 1               5                  10                  15

<210> SEQ ID NO 138
<211> LENGTH: 16
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(16)
<223> OTHER INFORMATION: Xaa=any amino acid

<400> SEQUENCE: 138

Gly Pro Arg Val Val Xaa Xaa Xaa Xaa Xaa Xaa Xaa Xaa Xaa Xaa
 1               5                  10                  15

<210> SEQ ID NO 139
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 139

Gly His Arg Pro Leu Xaa Xaa Xaa Xaa Xaa Xaa Xaa Xaa Xaa Xaa
 1               5                  10                  15

Xaa

<210> SEQ ID NO 140
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 140

Gly Pro Arg Pro Leu Xaa Xaa Xaa Xaa Xaa Xaa Xaa Xaa Xaa Xaa
1               5                   10                  15

Xaa

<210> SEQ ID NO 141
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 141

Gly His Arg Val Leu Xaa Xaa Xaa Xaa Xaa Xaa Xaa Xaa Xaa Xaa
1               5                   10                  15

Xaa

<210> SEQ ID NO 142
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 142

Gly Pro Arg Val Leu Xaa Xaa Xaa Xaa Xaa Xaa Xaa Xaa Xaa Xaa
1               5                   10                  15

Xaa

<210> SEQ ID NO 143
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 143

Gly His Arg Pro Val Xaa Xaa Xaa Xaa Xaa Xaa Xaa Xaa Xaa Xaa
1               5                   10                  15

Xaa

<210> SEQ ID NO 144
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 144

Gly Pro Arg Pro Val Xaa Xaa Xaa Xaa Xaa Xaa Xaa Xaa Xaa Xaa
1               5                   10                  15

Xaa

<210> SEQ ID NO 145
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 145

Gly His Arg Val Val Xaa Xaa Xaa Xaa Xaa Xaa Xaa Xaa Xaa Xaa
 1               5                  10                  15

Xaa

<210> SEQ ID NO 146
<211> LENGTH: 17
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(17)
<223> OTHER INFORMATION: Xaa=any amino acid

<400> SEQUENCE: 146

Gly Pro Arg Val Val Xaa Xaa Xaa Xaa Xaa Xaa Xaa Xaa Xaa Xaa
 1               5                  10                  15

Xaa

<210> SEQ ID NO 147
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 147

Gly His Arg Pro Leu Xaa Xaa Xaa Xaa Xaa Xaa Xaa Xaa Xaa Xaa
 1               5                  10                  15

Xaa Xaa

<210> SEQ ID NO 148
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 148

Gly Pro Arg Pro Leu Xaa Xaa Xaa Xaa Xaa Xaa Xaa Xaa Xaa Xaa
 1               5                  10                  15

Xaa Xaa

```
<210> SEQ ID NO 149
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 149

Gly His Arg Val Leu Xaa Xaa Xaa Xaa Xaa Xaa Xaa Xaa Xaa Xaa
 1               5                  10                  15

Xaa Xaa

<210> SEQ ID NO 150
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 150

Gly Pro Arg Val Leu Xaa Xaa Xaa Xaa Xaa Xaa Xaa Xaa Xaa Xaa
 1               5                  10                  15

Xaa Xaa

<210> SEQ ID NO 151
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 151

Gly His Arg Pro Val Xaa Xaa Xaa Xaa Xaa Xaa Xaa Xaa Xaa Xaa
 1               5                  10                  15

Xaa Xaa

<210> SEQ ID NO 152
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 152

Gly Pro Arg Pro Val Xaa Xaa Xaa Xaa Xaa Xaa Xaa Xaa Xaa Xaa
 1               5                  10                  15

Xaa Xaa

<210> SEQ ID NO 153
<211> LENGTH: 18
```

```
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 153

Gly His Arg Val Val Xaa Xaa Xaa Xaa Xaa Xaa Xaa Xaa Xaa Xaa
 1               5                  10                  15

Xaa Xaa

<210> SEQ ID NO 154
<211> LENGTH: 18
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(18)
<223> OTHER INFORMATION: Xaa=any amino acid

<400> SEQUENCE: 154

Gly Pro Arg Val Val Xaa Xaa Xaa Xaa Xaa Xaa Xaa Xaa Xaa Xaa
 1               5                  10                  15

Xaa Xaa

<210> SEQ ID NO 155
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 155

Gly His Arg Pro Leu Xaa Xaa Xaa Xaa Xaa Xaa Xaa Xaa Xaa Xaa
 1               5                  10                  15

Xaa Xaa Xaa

<210> SEQ ID NO 156
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 156

Gly Pro Arg Pro Leu Xaa Xaa Xaa Xaa Xaa Xaa Xaa Xaa Xaa Xaa
 1               5                  10                  15

Xaa Xaa Xaa

<210> SEQ ID NO 157
<211> LENGTH: 19
<212> TYPE: PRT
<213> ORGANISM: Artificial Sequence
<220> FEATURE:
```

```
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 157

Gly His Arg Val Leu Xaa Xaa Xaa Xaa Xaa Xaa Xaa Xaa Xaa Xaa
 1               5                  10                  15

Xaa Xaa Xaa

<210> SEQ ID NO 158
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 158

Gly Pro Arg Val Leu Xaa Xaa Xaa Xaa Xaa Xaa Xaa Xaa Xaa Xaa
 1               5                  10                  15

Xaa Xaa Xaa

<210> SEQ ID NO 159
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 159

Gly His Arg Pro Val Xaa Xaa Xaa Xaa Xaa Xaa Xaa Xaa Xaa Xaa
 1               5                  10                  15

Xaa Xaa Xaa

<210> SEQ ID NO 160
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 160

Gly Pro Arg Pro Val Xaa Xaa Xaa Xaa Xaa Xaa Xaa Xaa Xaa Xaa
 1               5                  10                  15

Xaa Xaa Xaa

<210> SEQ ID NO 161
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
```

```
<222> LOCATION: (6)...(19)
<223> OTHER INFORMATION: Xaa=any amino acid

<400> SEQUENCE: 161

Gly His Arg Val Val Xaa Xaa Xaa Xaa Xaa Xaa Xaa Xaa Xaa Xaa
 1               5                  10                  15

Xaa Xaa Xaa

<210> SEQ ID NO 162
<211> LENGTH: 19
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(19)
<223> OTHER INFORMATION: Xaa=any amino acid

<400> SEQUENCE: 162

Gly Pro Arg Val Val Xaa Xaa Xaa Xaa Xaa Xaa Xaa Xaa Xaa Xaa
 1               5                  10                  15

Xaa Xaa Xaa

<210> SEQ ID NO 163
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 163

Gly His Arg Pro Leu Xaa Xaa Xaa Xaa Xaa Xaa Xaa Xaa Xaa Xaa
 1               5                  10                  15

Xaa Xaa Xaa Xaa
            20

<210> SEQ ID NO 164
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 164

Gly Pro Arg Pro Leu Xaa Xaa Xaa Xaa Xaa Xaa Xaa Xaa Xaa Xaa
 1               5                  10                  15

Xaa Xaa Xaa Xaa
            20

<210> SEQ ID NO 165
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
```

```
<223> OTHER INFORMATION: Xaa=any amino acid

<400> SEQUENCE: 165

Gly His Arg Val Leu Xaa Xaa Xaa Xaa Xaa Xaa Xaa Xaa Xaa Xaa
1               5                   10                  15

Xaa Xaa Xaa Xaa
        20

<210> SEQ ID NO 166
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 166

Gly Pro Arg Val Leu Xaa Xaa Xaa Xaa Xaa Xaa Xaa Xaa Xaa Xaa
1               5                   10                  15

Xaa Xaa Xaa Xaa
        20

<210> SEQ ID NO 167
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 167

Gly His Arg Pro Val Xaa Xaa Xaa Xaa Xaa Xaa Xaa Xaa Xaa Xaa
1               5                   10                  15

Xaa Xaa Xaa Xaa
        20

<210> SEQ ID NO 168
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 168

Gly Pro Arg Pro Val Xaa Xaa Xaa Xaa Xaa Xaa Xaa Xaa Xaa Xaa
1               5                   10                  15

Xaa Xaa Xaa Xaa
        20

<210> SEQ ID NO 169
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
```

<222> LOCATION: (6)...(20)
<223> OTHER INFORMATION: Xaa=any amino acid

<400> SEQUENCE: 169

Gly His Arg Val Val Xaa Xaa Xaa Xaa Xaa Xaa Xaa Xaa Xaa Xaa
1               5                   10                  15

Xaa Xaa Xaa Xaa
            20

<210> SEQ ID NO 170
<211> LENGTH: 20
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(20)
<223> OTHER INFORMATION: Xaa=any amino acid

<400> SEQUENCE: 170

Gly Pro Arg Val Val Xaa Xaa Xaa Xaa Xaa Xaa Xaa Xaa Xaa Xaa
1               5                   10                  15

Xaa Xaa Xaa Xaa
            20

<210> SEQ ID NO 171
<211> LENGTH: 21
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(21)
<223> OTHER INFORMATION: Xaa=any amino acid

<400> SEQUENCE: 171

Gly His Arg Pro Leu Xaa Xaa Xaa Xaa Xaa Xaa Xaa Xaa Xaa Xaa
1               5                   10                  15

Xaa Xaa Xaa Xaa Xaa
            20

<210> SEQ ID NO 172
<211> LENGTH: 21
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(21)
<223> OTHER INFORMATION: Xaa=any amino acid

<400> SEQUENCE: 172

Gly Pro Arg Pro Leu Xaa Xaa Xaa Xaa Xaa Xaa Xaa Xaa Xaa Xaa
1               5                   10                  15

Xaa Xaa Xaa Xaa Xaa
            20

<210> SEQ ID NO 173
<211> LENGTH: 21
<212> TYPE: PRT
<213> ORGANISM: Artificial Sequence
<220> FEATURE:
<223> OTHER INFORMATION: peptide of formula II
<220> FEATURE:

```
<221> NAME/KEY: VARIANT
<222> LOCATION: (6)...(21)
<223> OTHER INFORMATION: Xaa=any amino acid

<400> SEQUENCE

```
<220> FEATURE:
<221> NAME/KEY: VARIANT
<222> LOCATION: (6)...(21)
<223> OTHER INFORMATION: Xaa=any amino acid

<400> SEQUENCE: 177

Gly His Arg Val Val Xaa Xaa Xaa Xaa Xaa Xaa Xaa Xaa Xaa Xaa
1               5                   10                  15

Xaa Xaa Xaa Xaa Xaa
            20

<210> SEQ ID NO 178
<211> LENGTH: 21
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(21)
<223> OTHER INFORMATION: Xaa=any amino acid

<400> SEQUENCE: 178

Gly Pro Arg Val Val Xaa Xaa Xaa Xaa Xaa Xaa Xaa Xaa Xaa Xaa
1               5                   10                  15

Xaa Xaa Xaa Xaa Xaa
            20

<210> SEQ ID NO 179
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 179

Gly His Arg Pro Leu Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 180
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 180

Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 181
<211> LENGTH: 22
<212> TYPE: PRT
<213> ORGANISM: Artificial Sequence
<220> FEATURE:
```

```
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 181

Gly His Arg Val Leu Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 182
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 182

Gly Pro Arg Val Leu Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 183
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 183

Gly His Arg Pro Val Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 184
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 184

Gly Pro Arg Pro Val Xaa Xaa Xaa Xaa Xaa Xaa Xaa Xaa Xaa Xaa Xaa
1               5                   10                  15

Xaa Xaa Xaa Xaa Xaa Xaa
            20

<210> SEQ ID NO 185
<211> LENGTH: 22
<212> TYPE: PRT
<213> ORGANISM: Artificial Sequence
```

```
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 185

Gly His Arg Val Val Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 186
<211> LENGTH: 22
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(22)
<223> OTHER INFORMATION: Xaa=any amino acid

<400> SEQUENCE: 186

Gly Pro Arg Val Val Xaa Xaa Xaa Xaa Xaa Xaa Xaa Xaa Xaa Xaa Xaa
 1               5                  10                  15

Xaa Xaa Xaa Xaa Xaa Xaa
            20

<210> SEQ ID NO 187
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 187

Gly His Arg Pro Leu Xaa Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 188
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 188

Gly Pro Arg Pro Leu Xaa Xaa Xaa Xaa Xaa Xaa Xaa Xaa Xaa Xaa Xaa
 1               5                  10                  15

Xaa Xaa Xaa Xaa Xaa Xaa Xaa
            20

<210> SEQ ID NO 189
<211> LENGTH: 23
<212> TYPE: PRT
```

```
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 189

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 190
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 190

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 191
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 191

Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 192
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 192

Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 193
<211> LENGTH: 23
```

```
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 193

Gly His Arg Val Val Xaa Xaa Xaa Xaa Xaa Xaa Xaa Xaa Xaa Xaa
  1               5                  10                  15

Xaa Xaa Xaa Xaa Xaa Xaa Xaa
             20

<210> SEQ ID NO 194
<211> LENGTH: 23
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(23)
<223> OTHER INFORMATION: Xaa=any amino acid

<400> SEQUENCE: 194

Gly Pro Arg Val Val Xaa Xaa Xaa Xaa Xaa Xaa Xaa Xaa Xaa Xaa
  1               5                  10                  15

Xaa Xaa Xaa Xaa Xaa Xaa Xaa
             20

<210> SEQ ID NO 195
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 195

Gly His Arg Pro Leu Xaa Xaa Xaa Xaa Xaa Xaa Xaa Xaa Xaa Xaa
  1               5                  10                  15

Xaa Xaa Xaa Xaa Xaa Xaa Xaa Xaa
             20

<210> SEQ ID NO 196
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 196

Gly Pro Arg Pro Leu Xaa Xaa Xaa Xaa Xaa Xaa Xaa Xaa Xaa Xaa
  1               5                  10                  15

Xaa Xaa Xaa Xaa Xaa Xaa Xaa Xaa
             20

<210> SEQ ID NO 197
```

```
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 197

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 198
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 198

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 199
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 199

Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 200
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 200

Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa
            20
```

```
<210> SEQ ID NO 201
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 201

Gly His Arg Val Val Xaa Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 202
<211> LENGTH: 24
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(24)
<223> OTHER INFORMATION: Xaa=any amino acid

<400> SEQUENCE: 202

Gly Pro Arg Val Val Xaa Xaa Xaa Xaa Xaa Xaa Xaa Xaa Xaa Xaa Xaa
 1               5                  10                  15

Xaa Xaa Xaa Xaa Xaa Xaa Xaa Xaa
            20

<210> SEQ ID NO 203
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 203

Gly His Arg Pro Leu Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 204
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 204

Gly Pro Arg Pro Leu Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25
```

-continued

```
<210> SEQ ID NO 205
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 205

Gly His Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 206
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 206

Gly Pro Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 207
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 207

Gly His Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 208
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 208

Gly Pro Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25
```

<210> SEQ ID NO 209
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 209

Gly His Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 210
<211> LENGTH: 25
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(25)
<223> OTHER INFORMATION: Xaa=any amino acid

<400> SEQUENCE: 210

Gly Pro Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa
            20                  25

<210> SEQ ID NO 211
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 211

Gly His Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa
            20                  25

<210> SEQ ID NO 212
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 212

Gly Pro Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa

-continued

```
            20                  25

<210> SEQ ID NO 213
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 213

Gly His Arg Val Leu Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 214
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 214

Gly Pro Arg Val Leu Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 215
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 215

Gly His Arg Pro Val Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 216
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 216

Gly Pro Arg Pro Val Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa
            20                  25

<210> SEQ ID NO 217
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 217

Gly His Arg Val Val Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 218
<211> LENGTH: 26
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(26)
<223> OTHER INFORMATION: Xaa=any amino acid

<400> SEQUENCE: 218

Gly Pro Arg Val Val Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 219
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 219

Gly His Arg Pro Leu Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 220
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 220

Gly Pro Arg Pro Leu Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa
            20                  25

<210> SEQ ID NO 221
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 221

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 222
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 222

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 223
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 223

Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 224
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 224

Gly Pro Arg Pro Val Xaa Xaa Xaa Xaa Xaa Xaa Xaa Xaa Xaa Xaa
```

```
1               5                  10                  15
Xaa Xaa Xaa Xaa Xaa Xaa Xaa Xaa Xaa Xaa Xaa
            20                  25

<210> SEQ ID NO 225
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 225

Gly His Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 226
<211> LENGTH: 27
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(27)
<223> OTHER INFORMATION: Xaa=any amino acid

<400> SEQUENCE: 226

Gly Pro Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa
            20                  25

<210> SEQ ID NO 227
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 227

Gly His Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa
            20                  25

<210> SEQ ID NO 228
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 228
```

```
Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25
```

<210> SEQ ID NO 229
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 229

```
Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25
```

<210> SEQ ID NO 230
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 230

```
Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25
```

<210> SEQ ID NO 231
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 231

```
Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa
            20                  25
```

<210> SEQ ID NO 232
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 232

```
Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25
```

<210> SEQ ID NO 233
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 233

```
Gly His Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25
```

<210> SEQ ID NO 234
<211> LENGTH: 28
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(28)
<223> OTHER INFORMATION: Xaa=any amino acid

<400> SEQUENCE: 234

```
Gly Pro Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25
```

<210> SEQ ID NO 235
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 235

```
Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25
```

<210> SEQ ID NO 236
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid -continued

```
<400> SEQUENCE: 236

Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 237
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 237

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 238
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 238

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa
            20                  25

<210> SEQ ID NO 239
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 239

Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 240
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid
```

-continued

```
<400> SEQUENCE: 240

Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 241
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 241

Gly His Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 242
<211> LENGTH: 29
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(29)
<223> OTHER INFORMATION: Xaa=any amino acid

<400> SEQUENCE: 242

Gly Pro Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25

<210> SEQ ID NO 243
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 243

Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
```

```
<223> OTHER INFORMATION: Xaa=any amino acid

<400> SEQUENCE: 244

Gly Pro Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 245
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 245

Gly His Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 246
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 246

Gly Pro Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 247
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 247

Gly His Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

<210> SEQ ID NO 248
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
```

```
<222> LOCATION: (6)...(30)
<223> OTHER INFORMATION: Xaa=any amino acid

<400> SEQUENCE: 248

Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 249
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 249

Gly His Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 250
<211> LENGTH: 30
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(30)
<223> OTHER INFORMATION: Xaa=any amino acid

<400> SEQUENCE: 250

Gly Pro Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 251
<211> LENGTH: 31
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(31)
<223> OTHER INFORMATION: Xaa=any amino acid

<400> SEQUENCE: 251

Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 252
<211> LENGTH: 31
<212> TYPE: PRT
<213> ORGANISM: Artificial Sequence
<220> FEATURE:
<223> OTHER INFORMATION: peptide of formula II
<220> FEATURE:
```

```
<221> NAME/KEY: VARIANT
<222> LOCATION: (6)...(31)
<223> OTHER INFORMATION: Xaa=any amino acid

<400> SEQUENCE: 252

Gly Pro Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

<210> SEQ ID NO 253
<211> LENGTH: 31
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(31)
<223> OTHER INFORMATION: Xaa=any amino acid

<400> SEQUENCE: 253

Gly His Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

<210> SEQ ID NO 254
<211> LENGTH: 31
<212> TYPE: PRT
<213> ORGANISM: Artificial Sequence
<220> FEATURE:
<223> OTHER INFORMATION: peptide of formula II   Xaa=any amino acid
<220> FEATURE:
<221> NAME/KEY: VARIANT
<222> LOCATION: (6)...(31)
<223> OTHER INFORMATION: Xaa=any amino acid

<400> SEQUENCE: 254

Gly Pro Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

<210> SEQ ID NO 255
<211> LENGTH: 31
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(31)
<223> OTHER INFORMATION: Xaa=any amino acid

<400> SEQUENCE: 255

Gly His Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

<210> SEQ ID NO 256
<211> LENGTH: 31
<212> TYPE: PRT
<213> ORGANISM: Artificial Sequence
<220> FEATURE:
<223> OTHER INFORMATION: peptide of formula II
```

```
<220> FEATURE:
<221> NAME/KEY: VARIANT
<222> LOCATION: (6)...(31)
<223> OTHER INFORMATION: Xaa=any amino acid

<400> SEQUENCE: 256

Gly Pro Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 257
<211> LENGTH: 31
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(31)
<223> OTHER INFORMATION: Xaa=any amino acid

<400> SEQUENCE: 257

Gly His Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 258
<211> LENGTH: 31
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(31)
<223> OTHER INFORMATION: Xaa=any amino acid

<400> SEQUENCE: 258

Gly Pro Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 259
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 259

Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 260
<211> LENGTH: 32
<212> TYPE: PRT
<213> ORGANISM: Artificial Sequence
<220> FEATURE:
```

```
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 260

Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 261
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 261

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 262
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 262

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 263
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 263

Gly His Arg Pro Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

<210> SEQ ID NO 264
<211> LENGTH: 32
<212> TYPE: PRT
<213> ORGANISM: Artificial Sequence
```

<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 264

Gly Pro Arg Pro Val Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

<210> SEQ ID NO 265
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 265

Gly His Arg Val Val Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

<210> SEQ ID NO 266
<211> LENGTH: 32
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(32)
<223> OTHER INFORMATION: Xaa=any amino acid

<400> SEQUENCE: 266

Gly Pro Arg Val Val Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

<210> SEQ ID NO 267
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 267

Gly His Arg Pro Leu Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
             20                  25                  30

Xaa

<210> SEQ ID NO 268

```
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 268

Gly Pro Arg Pro Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa

<210> SEQ ID NO 269
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 269

Gly His Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa

<210> SEQ ID NO 270
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 270

Gly Pro Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa

<210> SEQ ID NO 271
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 271

Gly His Arg Pro Val Xaa Xaa Xaa Xaa Xaa Xaa Xaa Xaa Xaa Xaa
```

```
                1               5                  10                 15
Xaa Xaa Xaa Xaa Xaa Xaa Xaa Xaa Xaa Xaa Xaa Xaa Xaa Xaa Xaa
                        20                  25                  30

Xaa

<210> SEQ ID NO 272
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 272

Gly Pro Arg Pro Val Xaa Xaa Xaa Xaa Xaa Xaa Xaa Xaa Xaa Xaa
 1               5                  10                 15

Xaa Xaa Xaa Xaa Xaa Xaa Xaa Xaa Xaa Xaa Xaa Xaa Xaa Xaa Xaa
                        20                  25                  30

Xaa

<210> SEQ ID NO 273
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 273

Gly His Arg Val Val Xaa Xaa Xaa Xaa Xaa Xaa Xaa Xaa Xaa Xaa
 1               5                  10                 15

Xaa Xaa Xaa Xaa Xaa Xaa Xaa Xaa Xaa Xaa Xaa Xaa Xaa Xaa Xaa
                        20                  25                  30

Xaa

<210> SEQ ID NO 274
<211> LENGTH: 33
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(33)
<223> OTHER INFORMATION: Xaa=any amino acid

<400> SEQUENCE: 274

Gly Pro Arg Val Val Xaa Xaa Xaa Xaa Xaa Xaa Xaa Xaa Xaa Xaa
 1               5                  10                 15

Xaa Xaa Xaa Xaa Xaa Xaa Xaa Xaa Xaa Xaa Xaa Xaa Xaa Xaa Xaa
                        20                  25                  30

Xaa

<210> SEQ ID NO 275
<211> LENGTH: 34
<212> TYPE: PRT
<213> ORGANISM: Artificial Sequence
<220> FEATURE:
```

<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 275

Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 276
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 276

Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 277
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 277

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 278
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 278

Gly Pro Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 279
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 279

Gly His Arg Pro Val Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 280
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 280

Gly Pro Arg Pro Val Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 281
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)
<223> OTHER INFORMATION: Xaa=any amino acid

<400> SEQUENCE: 281

Gly His Arg Val Val Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 282
<211> LENGTH: 34
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(34)

<223> OTHER INFORMATION: Xaa=any amino acid

<400> SEQUENCE: 282

Gly Pro Arg Val Val Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa

<210> SEQ ID NO 283
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 283

Gly His Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 284
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 284

Gly Pro Arg Pro Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 285
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 285

Gly His Arg Val Leu Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa

-continued

```
                35

<210> SEQ ID NO 286
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 286

Gly Pro Arg Val Leu Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 287
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 287

Gly His Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 288
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 288

Gly Pro Arg Pro Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 289
<211> LENGTH: 35
<212> TYPE: PRT
<213> ORGANISM: Artificial Sequence
<220> FEATURE:
<223> OTHER INFORMATION: peptide of formula II
<220> FEATURE:
```

```
<221> NAME/KEY: VARIANT
<222> LOCATION: (6)...(35)
<223> OTHER INFORMATION: Xaa=any amino acid

<400> SEQUENCE: 289

Gly His Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 290
<211> LENGTH: 35
<212> TYPE: PRT
<213> ORGANISM: Artificial Sequence
<220> FEATURE:
<223> OTHER INFORMATION: peptide of formula II
<220> FEATURE:
<221> NAME/KEY: VARIANT
<222> LOCATION: (6)...(35)
<223> OTHER INFORMATION: Xaa=any amino acid

<400> SEQUENCE: 290

Gly Pro Arg Val Val Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35

<210> SEQ ID NO 291
<211> LENGTH: 23
<212> TYPE: PRT
<213> ORGANISM: Artificial Sequence
<220> FEATURE:
<223> OTHER INFORMATION: peptide of formula II

<400> SEQUENCE: 291

Asp Lys Lys Arg Glu Glu Ala Pro Ser Leu Arg Pro Ala Pro Pro
 1               5                  10                  15

Ile Ser Gly Gly Gly Tyr Arg
            20

<210> SEQ ID NO 292
<211> LENGTH: 23
<212> TYPE: PRT
<213> ORGANISM: Artificial Sequence
<220> FEATURE:
<223> OTHER INFORMATION: peptide of formula II

<400> SEQUENCE: 292

Glu Arg His Gln Ser Ala Cys Lys Asp Ser Asp Trp Pro Phe Cys
 1               5                  10                  15

Asp Glu Asp Trp Asn Tyr Lys
            20

<210> SEQ ID NO 293
<211> LENGTH: 28
<212> TYPE: PRT
<213> ORGANISM: Artificial Sequence
<220> FEATURE:
<223> OTHER INFORMATION: peptide Aalpha

<400> SEQUENCE: 293
```

```
Gly Pro Arg Val Val Glu Arg His Gln Ser Ala Cys Lys Asp Ser Asp
1               5                   10                  15

Trp Pro Phe Cys Ser Asp Glu Asp Trp Asn Tyr Lys
            20                  25

<210> SEQ ID NO 294
<211> LENGTH: 28
<212> TYPE: PRT
<213> ORGANISM: Artificial Sequence
<220> FEATURE:
<223> OTHER INFORMATION: peptide Bbeta

<400> SEQUENCE: 294

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg
            20                  25

<210> SEQ ID NO 295
<211> LENGTH: 19
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(19)
<223> OTHER INFORMATION: Xaa=any amino acid

<400> SEQUENCE: 295

Gly His Arg Xaa Xaa Xaa Xaa Xaa Xaa Xaa Xaa Xaa Xaa Xaa Xaa Xaa
1               5                   10                  15

Xaa Xaa Xaa

<210> SEQ ID NO 296
<211> LENGTH: 19
<212> TYPE: PRT
<213> ORGANISM: Artificial Sequence
<220> FEATURE:
<223> OTHER INFORMATION: peptide of formula I
<220> FEATURE:
<221> NAME/KEY: VARIANT
<222> LOCATION: (4)...(19)
<223> OTHER INFORMATION: Xaa=any amino acid

<400> SEQUENCE: 296

Gly Pro Arg Xaa Xaa Xaa Xaa Xaa Xaa Xaa Xaa Xaa Xaa Xaa Xaa Xaa
1               5                   10                  15

Xaa Xaa Xaa
```

THERAPEUTIC FIBRIN-DERIVED PEPTIDES AND USES THEREOF

CROSS REFERENCE TO RELATED APPLICATIONS

The present application is a continuation of U.S. patent application Ser. No. 10/459,030, filed Jun. 11, 2003, now U.S. Pat. No. 7,271,144, which is a continuation of International Patent Application No. PCT/AT01/00387, filed Dec. 7, 2001, published in German on Jun. 20, 2002 as International Patent Publication No. WO02/248180, which claims priority to Austrian Application No. AT A 2063/2000, filed Dec. 12, 2000, all of which are incorporated in their entireties herein.

BACKGROUND

The invention concerns peptides and/or proteins, their use for preparing a therapeutic and/or preventive pharmaceutical composition as well as a pharmaceutical composition.

Substances for the inhibition or prevention of inflammatory reactions, so-called immunosuppressants, which so far have been used for prophylaxis and therapy, generally comprise two distinct groups. Firstly, derivatives of a hormone, i.e. cortisone, naturally occurring in the body, and secondly, exogenous immunosuppressants such as cyclosporin and its derivatives, azathioprine, cyclophosphamide etc. All those substances possess anti-inflammatory effects but they show substantial side reactions in long-term therapy. Those side reactions have a limiting effect on long-term therapy, which is why those substances are used alternately or in combination in order to keep side effects on a tolerable level or in order to be able to actually proceed with the therapy. As examples of side reactions, the pathological fractures associated with cortisone are to be mentioned, which fractures are caused by the osteoporotic effect of the cortisone, or the renal failure which may be caused by cyclosporin. Those side reactions are inevitable with both groups of compounds, and hence it is merely a question of the duration of the therapy and of the total dose at what point the therapy must be stopped.

SUMMARY OF THE INVENTION

The present invention has as its object to provide new pharmaceutical products which are suitable for preventing or inhibiting inflammatory effects and which only show minor side effects. A further object consists in providing long-term therapy.

In the following, the amino acids of the peptides according to the invention are referred to by the usual abbreviations, which denote the α-amino acids.

By "analogues," a peptide is understood which, by derivatisation, substitution, preferably homologous substitution, deletion and/or insertion, is derived from the sequence of the fibrin and in particular from the preferred sequences.

The peptides or protein according to the invention exhibit the general formula I

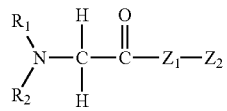

wherein $R_1$ and $R_2$, being equal or different, denote hydrogen, a saturated or unsaturated hydrocarbon residue comprising from 1 to 3, in particular up to 10, carbon atoms, $Z_1$ denotes a histidine or proline residue, $Z_2$ denotes an arginine residue, a peptide residue or a protein residue comprising an initial arginine residue, in particular comprising from 2 to 30 amino acids, as well as the salts thereof, and, f.i., also amides, or mixtures with each other and /or with at least one further substance for therapeutic and/or preventive use in human and/or veterinary medicine, whereby in particular only L-amino acids are provided. Sequences of formula I are listed in Table 1.

It was completely surprising that the specified amino acid sequence prevents the adhesion of cells from the bloodstream to endothelial cells of the vascular wall and/or their subsequent transmigration from the blood into the tissue.

The peptides or protein according to the invention exhibit the general formula II

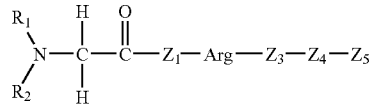

wherein $R_1$ and $R_2$, being equal or different, denote hydrogen, a saturated or unsaturated hydrocarbon residue comprising from 1 to 3, in particular up to 10, carbon atoms, $Z_1$ denotes a histidine or proline residue, Arg denotes an arginine, $Z_3$ denotes a proline or valine residue, $Z_4$ denotes a leucine or valine residue, $Z_5$ denotes a protein residue or a peptide residue, in particular comprising from 2 to 30 amino acids, or an alcohol comprising from 1 to 3, in particular up to 10, carbon atoms, or an organic or inorganic base residue, as well as the salts thereof, and, f.i., also amides, or mixtures with each other and/or with at least one further substance for therapeutic and/or preventive use in human and/or veterinary medicine, whereby in particular only L-amino acids are provided. Sequences of formula II are listed in Table 2.

It was completely surprising that parts of the sequence, peptides or fragments of the fibrinogen exhibit anti-inflammatory effects. Without being bound by such theoretical considerations, said effects might be based on the fact that the fibrin binds to endothelial cells via its neo-N-terminus of the Bbeta-chain and to cells in the bloodstream via the sequence of the Aalpha-chain, thereby leading to the adhesion and transmigration of cells into the tissue. Those bindings exhibit a side reaction in that the formation of fibrin is inhibited. However, said inhibition does not constitute a potential disadvantage to the patient since the blood coagulation is sufficient also in the absence of fibrin if slight injuries occur. Only in case of surgical treatment, it might optionally be suitable to stop such kind of therapy. Other side reactions may substantially be ruled out, since those substances only interact with natural ligands. Furthermore, the natural defense is not affected adversely by the leukocytes in the blood. Thus, the composition of the same, such as granulocytes, lymphocytes and monocytes, remains unaffected so that the natural defense process is maintained and the defense against infections in the blood remains unchanged.

DETAILED DESCRIPTION

Fibrinogen is produced in the liver and, in this form, is biologically inactive and normally is provided in the blood at concentrations of around 3 g/l. By proteolytic cleavage of the proenzyme prothrombin, thrombin is formed which cleaves off the fibrinopeptides A and B from the fibrinogen. In doing so, fibrinogen is transformed into its biologically active form. Fibrin and fibrin cleavage products are generated.

Thrombin is formed during each activation of the blood coagulation, i.e. with each damage to the tissue, be it of inflammatory, traumatic or degenerative genesis. The formation of fibrin as mediated by thrombin is basically a protective process with the purpose of quickly sealing any defects caused to the vascular system. However, the formation of fibrin is also a pathogenic process. The appearance of a fibrin thrombus as the triggering cause of cardiac infarction is one of the most prominent problems in human medicine.

The role which fibrin plays during the extravastation of inflammatory cells from the bloodstream into the tissue, which, on the one hand, is a desired process of the defense against pathogenic microorganisms or tumour cells occurring in the tissue, but, on the other hand, is a process which, by itself, induces or prolongues damage done to the tissue, has so far not been examined at all or not to a sufficient extent. Fibrin binds to endothelial cells via its neo-N-terminus of Bbeta by means of the sequence to Bbeta and to cells in the bloodstream by means of the sequence Aalpha, thereby leading to the adhesion and transmigration of cells into the tissue.

The peptides or proteins according to the invention may prevent the adhesion of cells from the bloodstream to endothelial cells of the vascular wall and/or their subsequent transmigration from the blood into the tissue.

A peptide or protein according to the invention of the general formula II, wherein $Z_5$ denotes a peptide residue comprising the following amino acid sequence (SEQ ID NO 291):

```
Asp Lys Lys Arg Glu Glu Ala Pro Ser Leu Arg Pro
Ala Pro Pro Pro Ile Ser Gly Gly Gly Tyr Arg
``` and
$Z_1$ denotes a histidine residue,
Arg denotes an arginine residue,
$Z_3$ denotes a proline residue,
$Z_4$ denotes a leucine residue, prevents fibrin fragments from depositing on or adhering to the vascular wall. Thus, it is rendered impossible that inflammatory cells are retained at the endothelial cells of the vascular walls of arteries and veins, and such cells are prevented from remaining at the vascular walls, thus being prevented from infiltrating the tissue any further.

A peptide or protein of the general formula II, wherein $Z_5$ denotes a peptide residue comprising the following amino acid sequence (SEQ ID NO 292):

```
Glu Arg His Gln Ser Ala Cys Lys Asp Ser Asp Trp
Pro Phe Cys Ser Asp Glu Asp Trp Asn Tyr Lys
``` and
$Z_1$ denotes a proline residue,
Arg denotes an arginine residue,
$Z_3$ denotes a valine residue,
$Z_4$ denotes a valine residue, has the effect of preventing the cells of the peripheral blood from adhering to fibrin or fibrin fragments, hence prohibiting their migration in the tissue.

The described cleavage products are also known in the literature as peptide Bbeta and peptide Aalpha. Said above mentioned proadhesive and promigratory path is a completely new one for the system of controlling the migration of cells from the blood into the tissue. This function of the fibrin may be blocked by peptide Bbeta and also by peptide Aalpha.

Therefore, said peptides according to the invention are suitable as therapeutic agents for humans and animals in order to block the migration of cells from the blood into the tissue. Since fibrin or other fibrinogen products produced by proteolytic cleavage, such as, f.i., fibrinogen cleaved by an urokinase-plasminogen-activator, are generated only to a specific and regionally limited extent, i.e. at sites of inflammation, disturbed coagulation, arterial sclerosis, thrombosis and/or tumour growth, the effect of said therapeutic agent is regionally limited, which means that pathological side effects occurring in other places are not to be expected or only to a limited extent.

Preferable and completely unexpected fields of application for the peptides and/or proteins according to the invention consist in the preparation of pharmaceutical compositions for the therapy or prevention of local and/or generalized inflammations in the body in case of infectious genesis, based upon an auto-immune reaction, based upon a rheumatic disease, based upon a disorder in the immune system, based upon a genetic disease, for the prevention and/or therapy of the rejection occurring after organ transplants, of arterial sclerosis, of a reperfusion trauma, based upon arteriosclerotic and/or thrombotic diseases and an increased fibrin deposition. Such a peptide, in particular Bbeta, is also excellently suitable for the preparation of a pharmaceutical composition which accomplishes the transportation of a further drug substance to human or animal endothelial cells. In doing so, the drug substance to be transported is coupled to the peptide at one end and then, via VE-cadherin, deposits on a free spot of the vascular wall, i.e. on an endothelial cell.

In the following, the invention is explained in further detail by way of examples.

EXAMPLES

Example 1

Preparation of the Fibrinogen Cleavage Products

Non-polymerizing degradation products of fibrinogen were obtained by means of a decomposition involving cyanogen bromide according to Blombäck et al. (Nature 1968, 218; 130-134). The fibrinogen thus degraded largely consists of a 63 kD fragment, i.e. the N-terminal disulfide knot, NDSK, and comprises Aalpha-chain 1-51, Bbeta-chain 1-118 and gamma-chain 1-78. In order to obtain NDSK-II (NDSK minus fibrinopeptides A and B), the N-terminal amino acids of the Aalpha- and Bbeta-chains were cleaved off with thrombin (20 units/1 µg NDSK) in three hours at room temperature and subsequently were treated with diisopropylfluorophosphate in order to block thrombin activity. The NDSK-II thus obtained consisted of Aalpha-chain 17-51, Bbeta-chain 15-118 and gamma-chain 1-78.

In order to obtain NDSK-uPA, 500 µg of NDSK was treated with 200 units of urokinase-plasminogen-activator (uPA) of Messrs. Technoclone, Vienna, Austria, for one hour at 37° C. The reaction was stopped with 5 mM phenylmethylsulfonyl fluoride. The NDSK-uPA thus obtained is a NDSK and has no fibrinopeptide B.

As a negative control, a second fraction was obtained from the fibrinogen cleavage products referred to as FCB-2 according to Nieuwenhuizen et al. (Biochem Biophys Acta 1983, 755; 531-533), which cleavage products were produced by being treated with cyanogen bromide. FCB-2 is a protein having a size of 43 kD and consists of Aalpha-chain 148-208, Bbeta-chain 191-305 and gamma-chain 95-265. For control purposes, thrombin and diisopropylfluorophosphate were added to said protein. That, however, did not result in any change to the protein (in the following, referred to as FCB-2-thr).

For the purpose of further negative controls, culture medium (RPMI of Messrs. Life techn. Inc., Paisky, UK) was treated with thrombin as above and, subsequently, was inactivated (RPMI-thr) or was treated with uPA as above and was inactivated (RPMI-uPA).

Example 2

Peptide Aalpha (SEQ ID NO 293) corresponds to amino acids 1 to 28 of the alpha-chain of the fibrin and is identical to amino acids 17 to 45 of the Aalpha-chain of the fibrinogen:

Gly Pro Arg Val Val Glu Arg His Gln Ser Ala Cys

Lys Asp Ser Asp Trp Pro Phe Cys Ser Asp Glu Asp

Trp Asn Tyr Lys

Peptide Bbeta (SEQ IN NO 294) corresponds to amino acids 1 to 28 of the beta-chain of the fibrin, which is identical to amino acids 15 to 43 of the Bbeta-chain of the fibrinogen, which exhibits the following sequence:

Gly His Arg Pro Leu Asp Lys Lys Arg Glu Glu Ala

Pro Ser Leu Arg Pro Ala Pro Pro Ile Ser Gly

Gly Gly Tyr Arg

By applying a fluorenylmethyloxycarbonyl (FMOC)-protective group strategy according to Carpino L. A. and Han. G Y, J. Amer. Chem. Soc. 1981; 37; 3404-3409, both peptides were synthesized by means of a solid-phase peptide synthesis according to Merrifield R. B., J. Amer. Chem. Soc. 1963; 85, 2149-2154, using a multiple peptide synthesizer. The crude peptides were purified by preparative reversed-phase HPLC via a Nucleosil 100-10, C18-column according to Engelhart H. and Müller H. Chromatography 1984 19:77 as well as Henschen A., Hupe K. P. and Lottspeich F. High Performance Liquid Chromatography VCH 1985. As control peptides, peptides of the same length but comprising a randomized amino acid sequence were used.

Example 3

HU-SCID Mouse-Model

Human skin was transplanted onto the backs of SCID mice, and two weeks later human lymphocytes were injected into the peritoneum. The proceedings were according to Petzelbauer et al. (J. Invest. Dermatol. 1996, 107; 576-581). Then, fifteen mice thus prepared were injected in their tail veins with the following:
a) 100 µg of human NDSK-II
b) 100 µg of human FCB-2
c) 100 µg of peptide Aalpha
d) 100 µg of peptide Bbeta
e) 100 µg of randomized Aalpha
f) 100 µg of randomized Bbeta Twenty-four hours later, the human skin was removed and the number of inflammatory sites, expressed in cells per 0.3 mm$^2$, was evaluated and the mean value was determined with a standard deviation.
For a: 22+/−2.8
for b: 9+/−2.1
for c: 4+/−1.1
for d: 6+/−1.1
for e: 5+/−1.2
for f: 7+/−1.3

That allows the conclusion that NDSK-II causes inflammations, and hence said protein was used as a pathogenic substance. The other compounds per se do not exhibit any significant increase in the amount of inflammatory cells.

Comparative Example 4

Fifteen mice according to Example 3 were injected in their tail veins with

100 µg of human NDSK-II and

100 µg of randomized peptide Aalpha.

Further proceedings were according to Example 3. Per 0.3 mm$^2$, 23+/−3.5 inflammatory sites could be determined.

Comparative Example 5

Fifteen mice according to Example 3 were injected in their tail veins with

100 µg of human NDSK-II according to Example 1 and

100 µg of randomized peptide Bbeta.

Further proceedings were according to Example 3. Per 0.3 mm$^2$, 24+/−2 inflammatory sites could be determined.

Example 6

Fifteen mice according to Example 3 were injected with

100 µg of human NDSK-II and

100 µg of synthesized peptide Aalpha.

Further proceedings were according to Example 3. Per 0.3 mm$^2$, 21+/−2.2 inflammatory sites could be determined.

Example 7

Fifteen mice according to Example 3 were injected in their tail veins with

100 µg of human NDSK-II and

100 µg of synthesized peptide Bbeta.

Further proceedings were according to Example 3. Per 0.3 mm$^2$, 14+/−2 inflammatory sites could be determined.

Examples 4 to 7 show that peptide Bbeta blocks lymphocytic inflammation.

Comparative Example 8

Endothelial cells from human umbilical veins (HUVEC) were marked with a red fluorescent dye (Cell Tracker Orange, 1 µl/ml, Molecular Probes, Eugene, Oreg.) and were dispersed on a collagen matrix (Collaborative Biomedical Products, Bedford, Mass.). Upon confluence of the endothelial cells, peripheral mononuclear blood cells (PBMC) ($10^5$ cells per 25 mm$^2$) marked with a green fluorescent dye (Cell Tracker Green, 1 μ/ml, Molecular Probes of Messrs. Eugene, Oreg.) were superimposed. Thereafter, the cells were incubated at 37°C. for twelve hours.

Adhering cells that had transmigrated into the gel were photographed with a laser-scan microscope, were converted into pixels and were evaluated by means of an 'NIH image" according to Gröger et al. (J. Immunol. Method 1999; 222: 101-109).

It was feasible to determine the number of adherent cells per 0.1 mm$^2$ such as mentioned under "adhesion." It was feasible to determine the number of migrated cells per 0.04 mm$^3$ such as mentioned under "migration." The mean value of three times three trials was evaluated together with the standard deviation.

|              |            | adhesion   | migration  |
|--------------|------------|------------|------------|
| a) RPMI-uPA  | 0.1 μg/ml  | 40 +/– 4   | 4 +/– 3    |
|              | 1.0 μg/ml  | 38 +/– 2   | 5 +/– 2    |
|              | 10.0 μg/ml | 32 +/– 4   | 5 +/– 1    |
| b) NDSK      | 0.1 μg/ml  | 31 +/– 18  | 6 +/– 3    |
|              | 1.0 μg/ml  | 35 +/– 18  | 5 +/– 2    |
|              | 10.0 μg/ml | 36 +/– 24  | 6 +/– 3    |
| c) NDSK-II   | 0.1 μg/ml  | 55 +/– 21  | 12 +/– 5   |
|              | 1.0 μg/ml  | 67 +/– 31  | 19 +/– 12  |
|              | 10.0 μg/ml | 65 +/– 31  | 19 +/– 10  |
| d) NDSK-uPA  | 0.1 μg/ml  | 58 +/– 3   | 10 +/– 2   |
|              | 1.0 μg/ml  | 60 +/– 3.5 | 14 +/– 3   |
|              | 10.0 μg/ml | 65 +/– 3   | 18 +/– 1.5 |
| e) FCB2      | 0.1 μg/ml  | 30 +/– 26  | 6 +/– 4    |
|              | 1.0 μg/ml  | 10 +/– 10  | 3 +/– 2    |
|              | 10.0 μg/ml | 21 +/– 7   | 5 +/– 4    |
| f) FCB-2-thr | 0.1 μg/ml  | 20 +/– 12  | 6 +/– 5    |
|              | 1.0 μg/ml  | 23 +/– 13  | 7 +/– 5    |
|              | 10.0 μg/ml | 26 +/– 11  | 4 +/– 2    |
| g) RPMI-thr  | 0.1 μg/ml  | 29 +/– 15  | 4 +/– 5    |
|              | 1.0 μg/ml  | 26 +/– 14  | 5 +/– 5    |
|              | 10.0 μg/ml | 41 +/– 20  | 5 +/– 4    |

That allows the conclusion that NDSK-II results in significant migrations of peripheral blood-monocellular cells (PBMC) to a greater extent than NDSK-uPA and hence exhibits pathogenic activity. None of the controls a), b), e), f) and g) resulted in any significant migration.

Example 9

100 μg of NDSK-II and Bbeta or Bbeta randomized were added to the collagen matrix according to Example 8 comprising the suspension of PBMC, and further proceedings were in accordance with Example 8.

|                                          | adhesion   | migration |
|------------------------------------------|------------|-----------|
| a) no addition of NDSK-II                | 38 +/– 15  | 6 +/– 4   |
| b) only 100 μg of NDSK-II                | 73 +/– 29  | 16 +/– 7  |
| c) 10 μg of Bbeta + NDSK-II              | 63 +/– 33  | 7 +/– 4   |
| d) 100 μg of Bbeta + NDSK-II             | 47 +/– 34  | 5 +/– 4   |
| e) 1000 μg of Bbeta + NDSK-II            | 52 +/– 27  | 10 +/– 6  |
| f) 10 μg of Bbeta randomized + NDSK-II   | 77 +/– 33  | 16 +/– 6  |
| g) 100 μg of Bbeta randomized + NDSK-II  | 86 +/– 35  | 15 +/– 6  |
| h) 1000 μg of Bbeta randomized + NDSK-II | 78 +/– 31  | 13 +/– 8  |

As can be gathered from those test results, peptide Bbeta blocks inflammations.

Example 10

100 μg of NDSK-II and Aalpha or Aalpha randomized were added to the collagen matrix according to Example 8 comprising the suspension of PBMC, and further proceedings were in accordance with Example 8.

|                                           | adhesion  | migration |
|-------------------------------------------|-----------|-----------|
| a) no addition of NDSK-II                 | 42 +/– 6  | 10 +/– 1  |
| b) only NDSK-II                           | 96 +/– 11 | 24 +/– 3  |
| c) 10 μg of Aalpha + NDSK-II              | 69 +/– 12 | 21 +/– 4  |
| d) 100 μg of Aalpha + NDSK-II             | 73 +/– 13 | 15 +/– 6  |
| e) 1000 μg of Aalpha + NDSK-II            | 70 +/– 6  | 13 +/– 5  |
| f) 10 μg of Aalpha randomized + NDSK-II   | 70 +/– 6  | 25 +/– 2  |
| g) 100 μg of Aalpha randomized + NDSK-II  | 65 +/– 16 | 24 +/– 3  |
| h) 1000 μg of Aalpha randomized + NDSK-II | 70 +/– 12 | 26 +/– 3  |

As can be gathered from the test results, peptide Aalpha blocks the migration of PBMC only partially.

Example 11

Since PBMC substantially consists of a mixture of lymphocytes and monocytes, pure lymphocytes instead of PBMC (as in Examples 8-10) were used in Example 11.

100 μg of NDSK-uPA or 100 μg of NDSK-II, respectively, and Aalpha or Bbeta, respectively, were added to the collagen matrix according to Example 8 comprising endothelial cells and lymphocytes.

|                                          | adhesion   | migration |
|------------------------------------------|------------|-----------|
| a) no addition                           | 68 +/– 8   | 16 +/– 3  |
| b) NDSK-uPA                              | 143 +/– 11 | 53 +/– 5  |
| c) NDSK-II                               | 119 +/– 11 | 43 +/– 4  |
| d) only 100 μg of Bbeta                  | 58 +/– 18  | 14 +/– 1  |
| e) NDSK-uPA + 100 μg of Bbeta            | 74 +/– 8   | 19 +/– 2  |
| f) NDSK-II + 100 μg of Bbeta             | 74 +/– 8   | 17 +/– 3  |
| g) only 100 μg of Aalpha                 | 77 +/– 4   | 18 +/– 1  |
| h) NDSK-uPA + 100 μg of Aalpha           | 131 +/– 4  | 40 +/– 3  |
| i) NDSK-II + 100 μg of Aalpha            | 131 +/– 4  | 44 +/– 4  |
| j) only 100 μg of Bbeta randomized       | 75 +/– 5   | 19 +/– 1  |
| k) NDSK-uPA + 100 μg of Bbeta randomized | 134 +/– 13 | 46 +/– 4  |
| l) NDSK-II + 100 μg of Bbeta randomized  | 120 +/– 12 | 42 +/– 4  |

Those test results show
1) that both NDSK-II and NDSK-uPA promote lymphocytic inflammation,
2) that peptide Bbeta completely blocks the lymphocytic adhesion and migration induced by NDSK-II and NDSK-uPA, whereas peptide Aalpha exhibits no blocking activity, which suggests that the free alpha-chain is not required for inducing the adhesion and migration of the lymphocytes.

Example 12

The proceedings were in accordance with Example 11, except for pure monocytes being used instead of lymphocytes. 100 μg of NDSK-uPA or 100 μg of NDSK-II, respectively, was added to peptide Aalpha, randomized Aalpha, Bbeta or randomized Bbeta.

|  | adhesion | migration |
|---|---|---|
| a) no addition | 43 +/− 8 | 7 +/− 1 |
| b) NDSK-uPA | 48 +/− 10 | 10 +/− 2 |
| c) NDSK-II | 90 +/− 11 | 19 +/− 6 |
| d) 100 μg of Bbeta | 59 +/− 7 | 5 +/− 1 |
| e) NDSK-uPA + 100 μg of Bbeta | 61 +/− 11 | 8 +/− 3 |
| f) NDSK-II + 100 μg of Bbeta | 70 +/− 7 | 7 +/− 5 |
| g) 100 μg of Bbeta randomized | 40 +/− 7 | 6 +/− 1 |
| h) NDSK-uPA + 100 μg of Bbeta randomized | 45 +/− 5 | 8 +/− 3 |
| g) NDSK-II + 100 μg of Bbeta randomized | 92 +/− 10 | 20 +/− 7 |
| j) 100 μg of Aalpha | 59 +/− 6 | 5 +/− 1 |
| k) NDSK-uPA + 100 μg of Aalpha | 62 +/− 4 | 8 +/− 5 |
| l) NDSK-II + 100 μg of Aalpha | 68 +/− 10 | 9 +/− 6 |
| m) 100 μg of Aalpha randomized | 58 +/− 7 | 6 +/− 1 |
| n) NDSK-uPA + 100 μg of Aalpha randomized | 50 +/− 10 | 10 +/− 4 |
| o) NDSK-II + 100 μg of Aalpha randomized | 108 +/− 8 | 21 +/− 5 |

Those test results show that only NDSK-II and not NDSK-uPA promotes the migration of monocytes, which means that both the alpha-chain and the beta-chain have to exhibit a free N-terminal end and block the migration of the monocytes.

Example 13

The proceedings were in accordance with Example 11, with pure lymphocytes being used. 100 μg of NDSK-uPA or 100 μg of NDSK-II, respectively, was added to the short peptide salts derived from Aalpha Gly Pro Arg (Pro)—NH₂ acetate (Aalpha derivative) or derived from Bbeta Gly His Arg Pro-OH acetate (Bbeta derivative).

|  | adhesion | migration |
|---|---|---|
| a) no addition | 60 +/− 8 | 14 +/− 1 |
| b) NDSK-uPA | 149 +/− 12 | 57 +/− 5 |
| c) NDSK-II | 121 +/− 11 | 48 +/− 7 |
| d) only 100 μg of Bbeta derivative | 58 +/− 10 | 12 +/− 9 |
| e) NDSK-uPA + 100 μg of Bbeta derivative | 70 +/− 8 | 16 +/− 3 |
| f) NDSK-II + 100 μg of Bbeta derivative | 69 +/− 7 | 14 +/− 5 |
| g) only 100 μg of Aalpha derivative | 77 +/− 4 | 18 +/− 1 |
| h) NDSK-uPA + 100 μg of Aalpha derivative | 134 +/− 4 | 48 +/− 5 |
| i) NDSK-II + 100 μg of Aalpha derivative | 131 +/− 7 | 49 +/− 6 |
| j) only 100 μg of Bbeta derivative randomized | 70 +/− 5 | 14 +/− 7 |
| k) NDSK-uPA + 100 μg of Bbeta derivative randomized | 130 +/− 12 | 49 +/− 6 |
| l) NDSK-II + 100 μg of Bbeta derivative randomized | 120 +/− 10 | 55 +/− 8 |

Said experiment allows the conclusion that, if lymphocytic migration is inhibited, those short peptides, added continuously in an appropriate manner, exhibit the same activity as do the long peptides.

Example 14

The proceedings were in accordance with Example 12, with pure monocytes being used. 100 mg of NDSK-uPA or 100 μg of NDSK-II, respectively, was added to the short peptide salts Aalpha Gly Pro Arg (Pro)—NH₂ acetate (Aalpha derivative) or Bbeta Gly His Arg Pro-OH acetate (Bbeta derivative).

|  | adhesion | migration |
|---|---|---|
| a) no addition | 40 +/− 8 | 5 +/− 1 |
| b) NDSK-uPA | 54 +/− 9 | 7 +/− 2 |
| c) NDSK-II | 85 +/− 11 | 22 +/− 6 |
| d) 100 μg of Bbeta derivative | 52 +/− 7 | 6 +/− 1 |
| e) NDSK-uPA + 100 μg of Bbeta derivative | 61 +/− 11 | 8 +/− 3 |
| f) NDSK-II + 100 μg of Bbeta derivative | 68 +/− 7 | 8 +/− 4 |
| g) 100 μg of Bbeta derivative randomized | 40 +/− 7 | 6 +/− 1 |
| h) NDSK-uPA + 100 μg of Bbeta derivative randomized | 44 +/− 6 | 8 +/− 2 |
| i) NDSK-II + 100 μg of Bbeta derivative randomized | 92 +/− 10 | 23 +/− 7 |
| j) 100 μg of Aalpha derivative | 50 +/− 5 | 4 +/− 4 |
| k) NDSK-uPA + 100 μg of Aalpha derivative | 60 +/− 5 | 7 +/− 6 |
| l) NDSK-II + 100 μg of Aalpha derivative | 64 +/− 11 | 8 +/− 2 |
| m) 100 μg of Aalpha derivative randomized | 54 +/− 10 | 6 +/− 3 |
| n) NDSK-uPA + 100 μg of Aalpha derivative randomized | 50 +/− 10 | 10 +/− 4 |
| o) NDSK-II + 100 μg of Aalpha derivative randomized | 99 +/− 8 | 21 +/− 7 |

Said experiment allows the conclusion that, if monocytic migration is inhibited, those short peptides, added continuously in an appropriate manner, exhibit the same activity as do the long peptides.

Example 15

The tests were carried out on male wistar rats weighing between 220 g and 280 g. The rats were given standard food and water. For carrying out the test, the rats were anaesthetized and artifically respirated with a frequency of 70 pulses per minute, whereby from 8 ml to 10 ml per kilogram of a gas containing 30 % by volume of oxygen and having an overpressure of from 1 mm to 2 mm mercury was emitted. The cardiac artery on the right hand side was equipped with a measuring cannula, and the blood pressure in the artery as well as the heartbeats were determined. The pressure rate was determined as a product of the blood pressure in the artery and of the heartbeat rate with the dimension mm mercury/minute/$10^3$. The vein on the right hand side was equipped with a measuring cannula for doping the test substances. After carrying out the surgical treatment, 2 ml of rat blood was supplied to the heart. Thirty minutes later, the cardiac artery on the left hand side was occluded. Another twenty-five minutes later, the occlusion was released in order to resupply the ischaemic area with blood. At that point of time, 800 μg/kg of peptide Bbeta or peptide Bbeta randomized, respectively, was intravenously administered to half of the animals, and then two hours were allowed to pass.

In order to distinguish between damaged and undamaged cardiac tissue, the cardiac artery on the left hand side was then supplied with evans blue dye at a concentration of 2% by weight. Thereupon, the removed heart was dissected by five horizontal cuts, the right hand wall of the vein was removed and the sections were treated with triphenyltetratolchloride (1% by weight) for twenty minutes at 37° C. so as to be able to distinguish between normal tissue and infarct tissue. The sections were evaluated by computer-sustained planimetry.

Because of the vascular occlusion, 62.5% of the cardiac muscle in the hearts of the reference rats was threatened, as opposed to 60% in the hearts of the test rats. In the hearts of the reference rats, 46% of the endangered tissue was dead, as opposed to 29% in the hearts of the test rats. That corresponds to a 37% reduction of dead tissue ($p<0.05$).

The substances according to the invention as well as the use of the substances according to the invention for preparing a pharmaceutical composition are of special significance:

For a pharmaceutical composition used in the therapy of diseases caused by the tissue-damaging effect of autoreactive lymphocytes.

Among those are diseases fitting into the sphere of autoimmunity, such as collagenoses, rheumatic diseases, psoriasis and post-/parainfectious diseases and diseases caused by a graft versus host reaction. A healing effect occurs, since said pharmaceutical composition blocks the migration of lymphocytes into the tissue. Thus, the lymphocytes remain in the bloodstream and are incapable of producing an autoreactive tissue-damaging effect.

A healing effect occurs with a drug for the therapy and/or prevention of the rejection occurring after organ transplants, since said drug prevents the migration of lymphocytes from the bloodstream into the foreign organ and hence the foreign organ cannot be destroyed by autoreactive lymphocytes.

A healing effect occurs with a drug for the therapy and/or prevention of arterial sclerosis after organ transplants, since said drug prohibits the migration of lymphocytes and monocytes into the vascular wall and hence prevents the activation of the cells of the vascular wall. In doing so, the occurrence of arterial sclerosis following organ transplants is minimized or prevented.

A healing effect occurs with a drug for the therapy and/or prevention of a reperfusion trauma following a surgically or pharmaceutically induced restoration of the blood flow such as, f.i. after cardiac infarction, apoplectic stroke, after vascular surgery, bypass surgery and organ transplants, since said drug inhibits the migration of lymphocytes and monocytes into the vascular wall. The reperfusion trauma is caused by oxygen deficiency/acidosis occurring in the cells of the vessel during the restoration of the blood flow and leads to their activation. Thereby, lymphocytes and monocytes adhere to the vascular wall and migrate into the same. The fact that lymphocytes and monocytes are prevented from adhering to and migrating into the vascular wall brings about a decrease in the hypoxia/acidosis-induced damage, without any permanent vascular damage being caused by the subsequent inflammatory reaction.

A healing effect occurs with a drug for the therapy and/or prevention of arterial sclerosis following metabolic diseases or ageing processes, since said drug inhibits the migration of lymphocytes and monocytes into the vascular wall and hence inhibits the progredience of the arteriosclerotic plaque resulting therefrom.

The pharmaceutical composition according to the invention may also be used for transporting a further drug substance. The pharmaceutical composition according to the invention specifically binds a surface molecule to endothelial cells. Thus, drug substances coupled thereto may be contacted with endothelial cells at high concentrations, without them being able to trigger side reactions in other places. The use of substances inhibiting cell division may be mentioned as an example, which substances may exhibit an antiangiogenetic effect after having been adducted specifically to endothelial cells. In that case, tumour patients experience a healing effect, since the growth of the tumour is blocked by preventing the proliferation of endothelial cells and hence by avoiding neoangiogenesis.

TABLE 1

Peptides of Formula I: Gly - His/Pro - Arg - Xaa$_2$ - Xaa$_{20}$

| SEQUENCE | SEQ ID NO |
|---|---|
| Gly His Arg | 1 |
| Gly Pro Arg | 2 |
| Gly His Arg Xaa | 3 |
| Gly Pro Arg Xaa | 4 |
| Gly His Arg Xaa Xaa | 5 |
| Gly Pro Arg Xaa Xaa | 6 |
| Gly His Arg Xaa Xaa Xaa | 7 |
| Gly Pro Arg Xaa Xaa Xaa | 8 |
| Gly His Arg Xaa Xaa Xaa Xaa | 9 |
| Gly Pro Arg Xaa Xaa Xaa Xaa | 10 |
| Gly His Arg Xaa Xaa Xaa Xaa Xaa | 11 |
| Gly Pro Arg Xaa Xaa Xaa Xaa Xaa | 12 |
| Gly His Arg Xaa Xaa Xaa Xaa Xaa Xaa | 13 |
| Gly Pro Arg Xaa Xaa Xaa Xaa Xaa Xaa | 14 |
| Gly His Arg Xaa Xaa Xaa Xaa Xaa Xaa Xaa | 15 |
| Gly Pro Arg Xaa Xaa Xaa Xaa Xaa Xaa Xaa | 16 |
| Gly His Arg Xaa Xaa Xaa Xaa Xaa Xaa Xaa Xaa | 17 |
| Gly Pro Arg Xaa Xaa Xaa Xaa Xaa Xaa Xaa Xaa | 18 |

TABLE 1-continued

Peptides of Formula I: Gly - His/Pro - Arg - Xaa$_2$ - Xaa$_{29}$

| SEQUENCE | SEQ ID NO |
|---|---|
| Gly His Arg Xaa Xaa Xaa Xaa Xaa Xaa Xaa Xaa | 19 |
| Gly Pro Arg Xaa Xaa Xaa Xaa Xaa Xaa Xaa Xaa | 20 |
| Gly His Arg Xaa Xaa Xaa Xaa Xaa Xaa Xaa Xaa Xaa | 21 |
| Gly Pro Arg Xaa Xaa Xaa Xaa Xaa Xaa Xaa Xaa Xaa | 22 |
| Gly His Arg Xaa Xaa Xaa Xaa Xaa Xaa Xaa Xaa Xaa Xaa | 23 |
| Gly Pro Arg Xaa Xaa Xaa Xaa Xaa Xaa Xaa Xaa Xaa Xaa | 24 |
| Gly His Arg Xaa Xaa Xaa Xaa Xaa Xaa Xaa Xaa Xaa Xaa Xaa | 25 |
| Gly Pro Arg Xaa Xaa Xaa Xaa Xaa Xaa Xaa Xaa Xaa Xaa Xaa | 26 |
| Gly His Arg Xaa Xaa Xaa Xaa Xaa Xaa Xaa Xaa Xaa Xaa Xaa Xaa | 27 |
| Gly Pro Arg Xaa Xaa Xaa Xaa Xaa Xaa Xaa Xaa Xaa Xaa Xaa Xaa | 28 |
| Gly His Arg Xaa Xaa Xaa Xaa Xaa Xaa Xaa Xaa Xaa Xaa Xaa Xaa Xaa | 29 |
| Gly Pro Arg Xaa Xaa Xaa Xaa Xaa Xaa Xaa Xaa Xaa Xaa Xaa Xaa Xaa | 30 |
| Gly His Arg Xaa Xaa Xaa Xaa Xaa Xaa Xaa Xaa Xaa Xaa Xaa Xaa Xaa Xaa | 31 |
| Gly Pro Arg Xaa Xaa Xaa Xaa Xaa Xaa Xaa Xaa Xaa Xaa Xaa Xaa Xaa Xaa | 32 |
| Gly His Arg Xaa Xaa Xaa Xaa Xaa Xaa Xaa Xaa Xaa Xaa Xaa Xaa Xaa Xaa Xaa | 33 |
| Gly Pro Arg Xaa Xaa Xaa Xaa Xaa Xaa Xaa Xaa Xaa Xaa Xaa Xaa Xaa Xaa Xaa | 34 |
| Gly His Arg Xaa Xaa Xaa Xaa Xaa Xaa Xaa Xaa Xaa Xaa Xaa Xaa Xaa Xaa Xaa Xaa | 295 |
| Gly Pro Arg Xaa Xaa Xaa Xaa Xaa Xaa Xaa Xaa Xaa Xaa Xaa Xaa Xaa Xaa Xaa Xaa | 296 |
| Gly His Arg Xaa Xaa Xaa Xaa Xaa Xaa Xaa Xaa Xaa Xaa Xaa Xaa Xaa Xaa Xaa Xaa Xaa | 35 |
| Gly Pro Arg Xaa Xaa Xaa Xaa Xaa Xaa Xaa Xaa Xaa Xaa Xaa Xaa Xaa Xaa Xaa Xaa Xaa | 36 |
| Gly His Arg Xaa Xaa Xaa Xaa Xaa Xaa Xaa Xaa Xaa Xaa Xaa Xaa Xaa Xaa Xaa Xaa Xaa Xaa | 37 |
| Gly Pro Arg Xaa Xaa Xaa Xaa Xaa Xaa Xaa Xaa Xaa Xaa Xaa Xaa Xaa Xaa Xaa Xaa Xaa Xaa | 38 |
| Gly His Arg Xaa Xaa Xaa Xaa Xaa Xaa Xaa Xaa Xaa Xaa Xaa Xaa Xaa Xaa Xaa Xaa Xaa Xaa Xaa | 39 |
| Gly Pro Arg Xaa Xaa Xaa Xaa Xaa Xaa Xaa Xaa Xaa Xaa Xaa Xaa Xaa Xaa Xaa Xaa Xaa Xaa Xaa | 40 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa | 41 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa | 42 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa | 43 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa | 44 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 45 |

TABLE 1-continued

Peptides of Formula I: Gly - His/Pro - Arg - Xaa$_2$ - Xaa$_{29}$

| SEQUENCE | SEQ ID NO |
|---|---|
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa | 46 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa | 47 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa | 48 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 49 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 50 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 51 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 52 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 53 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 54 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 55 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 56 |
| Gly His Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 57 |
| Gly Pro Arg Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 58 |

TABLE 2

Peptides of Formula II: Gly - His/Pro - Arg - Pro/Val - Leu/Val - Xaa$_2$ - Xaa$_{30}$

| SEQUENCE | SEQ ID NO |
|---|---|
| Gly His Arg Pro Leu Xaa Xaa | 59 |
| Gly Pro Arg Pro Leu Xaa Xaa | 60 |
| Gly His Arg Val Leu Xaa Xaa | 61 |
| Gly Pro Arg Val Leu Xaa Xaa | 62 |
| Gly His Arg Pro Val Xaa Xaa | 63 |
| Gly Pro Arg Pro Val Xaa Xaa | 64 |
| Gly His Arg Val Val Xaa Xaa | 65 |
| Gly Pro Arg Val Val Xaa Xaa | 66 |
| Gly His Arg Pro Leu Xaa Xaa Xaa | 67 |
| Gly Pro Arg Pro Leu Xaa Xaa Xaa | 68 |
| Gly His Arg Val Leu Xaa Xaa Xaa | 69 |
| Gly Pro Arg Val Leu Xaa Xaa Xaa | 70 |
| Gly His Arg Pro Val Xaa Xaa Xaa | 71 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
|---|---|
| Gly Pro Arg Pro Val Xaa Xaa Xaa | 72 |
| Gly His Arg Val Val Xaa Xaa Xaa | 73 |
| Gly Pro Arg Val Val Xaa Xaa Xaa | 74 |
| Gly His Arg Pro Leu Xaa Xaa Xaa Xaa | 75 |
| Gly Pro Arg Pro Leu Xaa Xaa Xaa Xaa | 76 |
| Gly His Arg Val Leu Xaa Xaa Xaa Xaa | 77 |
| Gly Pro Arg Val Leu Xaa Xaa Xaa Xaa | 78 |
| Gly His Arg Pro Val Xaa Xaa Xaa Xaa | 79 |
| Gly Pro Arg Pro Val Xaa Xaa Xaa Xaa | 80 |
| Gly His Arg Val Val Xaa Xaa Xaa Xaa | 81 |
| Gly Pro Arg Val Val Xaa Xaa Xaa Xaa | 82 |
| Gly His Arg Pro Leu Xaa Xaa Xaa Xaa Xaa | 83 |
| Gly Pro Arg Pro Leu Xaa Xaa Xaa Xaa Xaa | 84 |
| Gly His Arg Val Leu Xaa Xaa Xaa Xaa Xaa | 85 |
| Gly Pro Arg Val Leu Xaa Xaa Xaa Xaa Xaa | 86 |
| Gly His Arg Pro Val Xaa Xaa Xaa Xaa Xaa | 87 |
| Gly Pro Arg Pro Val Xaa Xaa Xaa Xaa Xaa | 88 |
| Gly His Arg Val Val Xaa Xaa Xaa Xaa Xaa | 89 |
| Gly Pro Arg Val Val Xaa Xa.a Xaa Xaa Xaa | 90 |
| Gly His Arg Pro Leu Xaa Xaa Xaa Xaa Xaa Xaa | 91 |
| Gly Pro Arg Pro Leu Xaa Xaa Xaa Xaa Xaa Xaa | 92 |
| Gly His Arg Val Leu Xaa Xaa Xaa Xaa Xaa Xaa | 93 |
| Gly Pro Arg Val Leu Xaa Xaa Xaa Xaa Xaa Xaa | 94 |
| Gly His Arg Pro Val Xaa Xaa Xaa Xaa Xaa Xaa | 95 |
| Gly Pro Arg Pro Val Xaa Xaa Xaa Xaa Xaa Xaa | 96 |
| Gly His Arg Val Val Xaa Xaa Xaa Xaa Xaa Xaa | 97 |
| Gly Pro Arg Val Val Xaa Xaa Xaa Xaa Xaa Xaa | 98 |
| Gly His Arg Pro Leu Xaa Xaa Xaa Xaa Xaa Xaa Xaa | 99 |
| Gly Pro Arg Pro Leu Xaa Xaa Xaa Xaa Xaa Xaa Xaa | 100 |
| Gly His Arg Val Leu Xaa Xaa Xaa Xaa Xaa Xaa Xaa | 101 |
| Gly Pro Arg Val Leu Xaa Xaa Xaa Xaa Xaa Xaa Xaa | 102 |
| Gly His Arg Pro Val Xaa Xaa Xaa Xaa Xaa Xaa Xaa | 103 |
| Gly Pro Arg Pro Val Xaa Xaa Xaa Xaa Xaa Xaa Xaa | 104 |
| Gly His Arg Val Val Xaa Xaa Xaa Xaa Xaa Xaa Xaa | 105 |
| Gly Pro Arg Val Val Xaa Xaa Xaa Xaa Xaa Xaa Xaa | 106 |
| Gly His Arg Pro Leu Xaa Xaa Xaa Xaa Xaa Xaa Xaa Xaa | 107 |
| Gly Pro Arg Pro Leu Xaa Xaa Xaa Xaa Xaa Xaa Xaa Xaa | 108 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
|---|---|
| Gly His Arg Val Leu Xaa Xaa Xaa Xaa Xaa Xaa Xaa Xaa | 109 |
| Gly Pro Arg Val Leu Xaa Xaa Xaa Xaa Xaa Xaa Xaa Xaa | 110 |
| Gly His Arg Pro Val Xaa Xaa Xaa Xaa Xaa Xaa Xaa Xaa | 111 |
| Gly Pro Arg Pro Val Xaa Xaa Xaa Xaa Xaa Xaa Xaa Xaa | 112 |
| Gly His Arg Val Val Xaa Xaa Xaa Xaa Xaa Xaa Xaa Xaa | 113 |
| Gly Pro Arg Val Val Xaa Xaa Xaa Xaa Xaa Xaa Xaa Xaa | 114 |
| Gly His Arg Pro Leu Xaa Xaa Xaa Xaa Xaa Xaa Xaa Xaa Xaa | 115 |
| Gly Pro Arg Pro Leu Xaa Xaa Xaa Xaa Xaa Xaa Xaa Xaa Xaa | 116 |
| Gly His Arg Val Leu Xaa Xaa Xaa Xaa Xaa Xaa Xaa Xaa Xaa | 117 |
| Gly Pro Arg Val Leu Xaa Xaa Xaa Xaa Xaa Xaa Xaa Xaa Xaa | 118 |
| Gly His Arg Pro Val Xaa Xaa Xaa Xaa Xaa Xaa Xaa Xaa Xaa | 119 |
| Gly Pro Arg Pro Val Xaa Xaa Xaa Xaa Xaa Xaa Xaa Xaa Xaa | 120 |
| Gly His Arg Val Val Xaa Xaa Xaa Xaa Xaa Xaa Xaa Xaa Xaa | 121 |
| Gly Pro Arg Val Val Xaa Xaa Xaa Xaa Xaa Xaa Xaa Xaa Xaa | 122 |
| Gly His Arg Pro Leu Xaa Xaa Xaa Xaa Xaa Xaa Xaa Xaa Xaa Xaa | 123 |
| Gly Pro Arg Pro Leu Xaa Xaa Xaa Xaa Xaa Xaa Xaa Xaa Xaa Xaa | 124 |
| Gly His Arg Val Leu Xaa Xaa Xaa Xaa Xaa Xaa Xaa Xaa Xaa Xaa | 125 |
| Gly Pro Arg Val Leu Xaa Xaa Xaa Xaa Xaa Xaa Xaa Xaa Xaa Xaa | 126 |
| Gly His Arg Pro Val Xaa Xaa Xaa Xaa Xaa Xaa Xaa Xaa Xaa Xaa | 127 |
| Gly Pro Arg Pro Val Xaa Xaa Xaa Xaa Xaa Xaa Xaa Xaa Xaa Xaa | 128 |
| Gly His Arg Val Val Xaa Xaa Xaa Xaa Xaa Xaa Xaa Xaa Xaa Xaa | 129 |
| Gly Pro Arg Val Val Xaa Xaa Xaa Xaa Xaa Xaa Xaa Xaa Xaa Xaa | 130 |
| Gly His Arg Pro Leu Xaa Xaa Xaa Xaa Xaa Xaa Xaa Xaa Xaa Xaa Xaa | 131 |
| Gly Pro Arg Pro Leu Xaa Xaa Xaa Xaa Xaa Xaa Xaa Xaa Xaa Xaa Xaa | 132 |
| Gly His Arg Val Leu Xaa Xaa Xaa Xaa Xaa Xaa Xaa Xaa Xaa Xaa Xaa | 133 |
| Gly Pro Arg Val Leu Xaa Xaa Xaa Xaa Xaa Xaa Xaa Xaa Xaa Xaa Xaa | 134 |
| Gly His Arg Pro Val Xaa Xaa Xaa Xaa Xaa Xaa Xaa Xaa Xaa Xaa Xaa | 135 |
| Gly Pro Arg Pro Val Xaa Xaa Xaa Xaa Xaa Xaa Xaa Xaa Xaa Xaa Xaa | 136 |
| Gly His Arg Val Val Xaa Xaa Xaa Xaa Xaa Xaa Xaa Xaa Xaa Xaa Xaa | 137 |
| Gly Pro Arg Val Val Xaa Xaa Xaa Xaa Xaa Xaa Xaa Xaa Xaa Xaa Xaa | 138 |
| Gly His Arg Pro Leu Xaa Xaa Xaa Xaa Xaa Xaa Xaa Xaa Xaa Xaa Xaa Xaa | 139 |
| Gly Pro Arg Pro Leu Xaa Xaa Xaa Xaa Xaa Xaa Xaa Xaa Xaa Xaa Xaa Xaa | 140 |
| Gly His Arg Val Leu Xaa Xaa Xaa Xaa Xaa Xaa Xaa Xaa Xaa Xaa Xaa Xaa | 141 |
| Gly Pro Arg Val Leu Xaa Xaa Xaa Xaa Xaa Xaa Xaa Xaa Xaa Xaa Xaa Xaa | 142 |
| Gly His Arg Pro Val Xaa Xaa Xaa Xaa Xaa Xaa Xaa Xaa Xaa Xaa Xaa Xaa | 143 |
| Gly Pro Arg Pro Val Xaa Xaa Xaa Xaa Xaa Xaa Xaa Xaa Xaa Xaa Xaa Xaa | 144 |
| Gly His Arg Val Val Xaa Xaa Xaa Xaa Xaa Xaa Xaa Xaa Xaa Xaa Xaa Xaa | 145 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
|---|---|
| Gly Pro Arg Val Val Xaa Xaa Xaa Xaa Xaa Xaa Xaa Xaa Xaa Xaa Xaa | 146 |
| Gly His Arg Pro Leu Xaa Xaa Xaa Xaa Xaa Xaa Xaa Xaa Xaa Xaa Xaa | 147 |
| Gly Pro Arg Pro Leu Xaa Xaa Xaa Xaa Xaa Xaa Xaa Xaa Xaa Xaa Xaa | 148 |
| Gly His Arg Val Leu Xaa Xaa Xaa Xaa Xaa Xaa Xaa Xaa Xaa Xaa Xaa | 149 |
| Gly Pro Arg Val Leu Xaa Xaa Xaa Xaa Xaa Xaa Xaa Xaa Xaa Xaa Xaa | 150 |
| Gly His Arg Pro Val Xaa Xaa Xaa Xaa Xaa Xaa Xaa Xaa Xaa Xaa Xaa | 151 |
| Gly Pro Arg Pro Val Xaa Xaa Xaa Xaa Xaa Xaa Xaa Xaa Xaa Xaa Xaa | 152 |
| Gly His Arg Val Val Xaa Xaa Xaa Xaa Xaa Xaa Xaa Xaa Xaa Xaa Xaa | 153 |
| Gly Pro Arg Val Val Xaa Xaa Xaa Xaa Xaa Xaa Xaa Xaa Xaa Xaa Xaa | 154 |
| Gly His Arg Pro Leu Xaa Xaa Xaa Xaa Xaa Xaa Xaa Xaa Xaa Xaa Xaa Xaa | 155 |
| Gly Pro Arg Pro Leu Xaa Xaa Xaa Xaa Xaa Xaa Xaa Xaa Xaa Xaa Xaa Xaa | 156 |
| Gly His Arg Val Leu Xaa Xaa Xaa Xaa Xaa Xaa Xaa Xaa Xaa Xaa Xaa Xaa | 157 |
| Gly Pro Arg Val Leu Xaa Xaa Xaa Xaa Xaa Xaa Xaa Xaa Xaa Xaa Xaa Xaa | 158 |
| Gly His Arg Pro Val Xaa Xaa Xaa Xaa Xaa Xaa Xaa Xaa Xaa Xaa Xaa Xaa | 159 |
| Gly Pro Arg Pro Val Xaa Xaa Xaa Xaa Xaa Xaa Xaa Xaa Xaa Xaa Xaa Xaa | 160 |
| Gly His Arg Val Val Xaa Xaa Xaa Xaa Xaa Xaa Xaa Xaa Xaa Xaa Xaa Xaa | 161 |
| Gly Pro Arg Val Val Xaa Xaa Xaa Xaa Xaa Xaa Xaa Xaa Xaa Xaa Xaa Xaa | 162 |
| Gly His Arg Pro Leu Xaa Xaa Xaa Xaa Xaa Xaa Xaa Xaa Xaa Xaa Xaa Xaa Xaa | 163 |
| Gly Pro Arg Pro Leu Xaa Xaa Xaa Xaa Xaa Xaa Xaa Xaa Xaa Xaa Xaa Xaa Xaa | 164 |
| Gly His Arg Val Leu Xaa Xaa Xaa Xaa Xaa Xaa Xaa Xaa Xaa Xaa Xaa Xaa Xaa | 165 |
| Gly Pro Arg Val Leu Xaa Xaa Xaa Xaa Xaa Xaa Xaa Xaa Xaa Xaa Xaa Xaa Xaa | 166 |
| Gly His Arg Pro Val Xaa Xaa Xaa Xaa Xaa Xaa Xaa Xaa Xaa Xaa Xaa Xaa Xaa | 167 |
| Gly Pro Arg Pro Val Xaa Xaa Xaa Xaa Xaa Xaa Xaa Xaa Xaa Xaa Xaa Xaa Xaa | 168 |
| Gly His Arg Val Val Xaa Xaa Xaa Xaa Xaa Xaa Xaa Xaa Xaa Xaa Xaa Xaa Xaa | 169 |
| Gly Pro Arg Val Val Xaa Xaa Xaa Xaa Xaa Xaa Xaa Xaa Xaa Xaa Xaa Xaa Xaa | 170 |
| Gly His Arg Pro Leu Xaa Xaa Xaa Xaa Xaa Xaa Xaa Xaa Xaa Xaa Xaa Xaa Xaa Xaa | 171 |
| Gly Pro Arg Pro Leu Xaa Xaa Xaa Xaa Xaa Xaa Xaa Xaa Xaa Xaa Xaa Xaa Xaa Xaa | 172 |
| Gly His Arg Val Leu Xaa Xaa Xaa Xaa Xaa Xaa Xaa Xaa Xaa Xaa Xaa Xaa Xaa Xaa | 173 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
| --- | --- |
| Gly Pro Arg Val Leu Xaa Xaa Xaa Xaa Xaa Xaa Xaa Xaa Xaa Xaa Xaa Xaa Xaa Xaa Xaa | 174 |
| Gly His Arg Pro Val Xaa Xaa Xaa Xaa Xaa Xaa Xaa Xaa Xaa Xaa Xaa Xaa Xaa Xaa Xaa | 175 |
| Gly Pro Arg Pro Val Xaa Xaa Xaa Xaa Xaa Xaa Xaa Xaa Xaa Xaa Xaa Xaa Xaa Xaa Xaa | 176 |
| Gly His Arg Val Val Xaa Xaa Xaa Xaa Xaa Xaa Xaa Xaa Xaa Xaa Xaa Xaa Xaa Xaa Xaa | 177 |
| Gly Pro Arg Val Val Xaa Xaa Xaa Xaa Xaa Xaa Xaa Xaa Xaa Xaa Xaa Xaa Xaa Xaa Xaa | 178 |
| Gly His Arg Pro Leu Xaa Xaa Xaa Xaa Xaa Xaa Xaa Xaa Xaa Xaa Xaa Xaa Xaa Xaa Xaa Xaa | 179 |
| Gly Pro Arg Pro Leu Xaa Xaa Xaa Xaa Xaa Xaa Xaa Xaa Xaa Xaa Xaa Xaa Xaa Xaa Xaa Xaa | 180 |
| Gly His Arg Val Leu Xaa Xaa Xaa Xaa Xaa Xaa Xaa Xaa Xaa Xaa Xaa Xaa Xaa Xaa Xaa Xaa | 181 |
| Gly Pro Arg Val Leu Xaa Xaa Xaa Xaa Xaa Xaa Xaa Xaa Xaa Xaa Xaa Xaa Xaa Xaa Xaa Xaa | 182 |
| Gly His Arg Pro Val Xaa Xaa Xaa Xaa Xaa Xaa Xaa Xaa Xaa Xaa Xaa Xaa Xaa Xaa Xaa Xaa | 183 |
| Gly Pro Arg Pro Val Xaa Xaa Xaa Xaa Xaa Xaa Xaa Xaa Xaa Xaa Xaa Xaa Xaa Xaa Xaa Xaa | 184 |
| Gly His Arg Val Val Xaa Xaa Xaa Xaa Xaa Xaa Xaa Xaa Xaa Xaa Xaa Xaa Xaa Xaa Xaa Xaa | 185 |
| Gly Pro Arg Val Val Xaa Xaa Xaa Xaa Xaa Xaa Xaa Xaa Xaa Xaa Xaa Xaa Xaa Xaa Xaa Xaa | 186 |
| Gly His Arg Pro Leu Xaa Xaa Xaa Xaa Xaa Xaa Xaa Xaa Xaa Xaa Xaa Xaa Xaa Xaa Xaa Xaa Xaa | 187 |
| Gly Pro Arg Pro Leu Xaa Xaa Xaa Xaa Xaa Xaa Xaa Xaa Xaa Xaa Xaa Xaa Xaa Xaa Xaa Xaa Xaa | 188 |
| Gly His Arg Val Leu Xaa Xaa Xaa Xaa Xaa Xaa Xaa Xaa Xaa Xaa Xaa Xaa Xaa Xaa Xaa Xaa Xaa | 189 |
| Gly Pro Arg Val Leu Xaa Xaa Xaa Xaa Xaa Xaa Xaa Xaa Xaa Xaa Xaa Xaa Xaa Xaa Xaa Xaa Xaa | 190 |
| Gly His Arg Pro Val Xaa Xaa Xaa Xaa Xaa Xaa Xaa Xaa Xaa Xaa Xaa Xaa Xaa Xaa Xaa Xaa Xaa | 191 |
| Gly Pro Arg Pro Val Xaa Xaa Xaa Xaa Xaa Xaa Xaa Xaa Xaa Xaa Xaa Xaa Xaa Xaa Xaa Xaa Xaa | 192 |
| Gly His Arg Val Val Xaa Xaa Xaa Xaa Xaa Xaa Xaa Xaa Xaa Xaa Xaa Xaa Xaa Xaa Xaa Xaa Xaa | 193 |
| Gly Pro Arg Val Val Xaa Xaa Xaa Xaa Xaa Xaa Xaa Xaa Xaa Xaa Xaa Xaa Xaa Xaa Xaa Xaa Xaa | 194 |
| Gly His Arg Pro Leu Xaa Xaa Xaa Xaa Xaa Xaa Xaa Xaa Xaa Xaa Xaa Xaa Xaa Xaa Xaa Xaa Xaa Xaa | 195 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa | 196 |
| Uty His Arg Val Leu Xaa Xaa Xaa Xaa Xaa Xaa Xaa Xaa Xaa Xaa Xaa Xaa Xaa Xaa Xaa Xaa Xaa Xaa | 197 |

TABLE 2-continued

Peptides of Formula II: Gly - His/Pro - Arg - Pro/Val - Leu/Val - $Xaa_2$ - $Xaa_{30}$

| SEQUENCE | SEQ ID NO |
|---|---|
| Gly Pro Arg Val Leu Xaa Xaa Xaa Xaa Xaa Xaa Xaa Xaa Xaa Xaa Xaa Xaa Xaa Xaa Xaa Xaa Xaa | 198 |
| Gly His Arg Pro Val Xaa Xaa Xaa Xaa Xaa Xaa Xaa Xaa Xaa Xaa Xaa Xaa Xaa Xaa Xaa Xaa | 199 |
| Gly Pro Arg Pro Val Xaa Xaa Xaa Xaa Xaa Xaa Xaa Xaa Xaa Xaa Xaa Xaa Xaa Xaa Xaa Xaa | 200 |
| Gly His Arg Val Val Xaa Xaa Xaa Xaa Xaa Xaa Xaa Xaa Xaa Xaa Xaa Xaa Xaa Xaa Xa.a Xaa | 201 |
| Gly Pro Arg Val Val Xaa Xaa Xaa Xaa Xaa Xaa Xaa Xaa Xaa Xaa Xaa Xaa Xaa Xaa Xaa Xaa | 202 |
| Gly His Arg Pro Leu Xaa Xaa Xaa Xaa Xaa Xaa Xaa Xaa Xaa Xaa Xaa Xaa Xaa Xaa Xaa Xaa Xaa | 203 |
| Gly Pro Arg Pro Leu Xaa Xaa Xaa Xaa Xaa Xaa Xaa Xaa Xaa Xaa Xaa Xaa Xaa Xaa Xaa Xaa Xaa | 204 |
| Gly His Arg Val Leu Xaa Xaa Xaa Xaa Xaa Xaa Xaa Xaa Xaa Xaa Xaa Xaa Xaa Xaa Xaa Xaa Xaa | 205 |
| Gly Pro Arg Val Leu Xaa Xaa Xaa Xaa Xaa Xaa Xaa Xaa Xaa Xaa Xaa Xaa Xaa Xaa Xaa Xaa Xaa | 206 |
| Gly His Arg Pro Val Xaa Xaa Xaa Xaa Xaa Xaa Xaa Xaa Xaa Xaa Xaa Xaa Xaa Xaa Xaa Xaa Xaa | 207 |
| Gly Pro Arg Pro Val Xaa Xaa Xaa Xaa Xaa Xaa Xaa Xaa Xaa Xaa Xaa Xaa Xaa Xaa Xaa Xaa Xaa | 208 |
| Gly His Arg Val Val Xaa Xaa Xaa Xaa Xaa Xaa Xaa Xaa Xaa Xaa Xaa Xaa Xaa Xaa Xaa Xaa Xaa | 209 |
| Gly Pro Arg Val Val Xaa Xaa Xaa Xaa Xaa Xaa Xaa Xaa Xaa Xaa Xaa Xaa Xaa Xaa Xaa Xaa Xaa | 210 |
| Gly His Arg Pro Leu Xaa Xaa Xaa Xaa Xaa Xaa Xaa Xaa Xaa Xaa Xaa Xaa Xaa Xaa Xaa Xaa Xaa Xaa | 211 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa | 212 |
| Gly His Arg Val Leu Xaa Xaa Xaa Xaa Xaa Xaa Xaa Xaa Xaa Xaa Xaa Xaa Xaa Xaa Xaa Xaa Xaa Xaa | 213 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa | 214 |
| Gly His Arg Pro Val Xaa Xaa Xaa Xaa Xaa Xaa Xaa Xaa Xaa Xaa Xaa Xaa Xaa Xaa Xaa Xaa Xaa Xaa | 215 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa | 216 |
| Gly His Arg Val Val Xaa Xaa Xaa Xaa Xaa Xaa Xaa Xaa Xaa Xaa Xaa Xaa Xaa Xaa Xaa Xaa Xaa Xaa | 217 |
| Gly Pro Arg Val Val Xaa Xaa Xaa Xaa Xaa Xaa Xaa Xaa Xaa Xaa Xaa Xaa Xaa Xaa Xaa Xaa Xaa Xaa | 218 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa | 219 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa | 220 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa | 221 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa | 222 |

TABLE 2-continued

Peptides of Formula II: Gly - His/Pro - Arg - Pro/Val - Leu/Val - $Xaa_2$ - $Xaa_{30}$

| SEQUENCE | SEQ ID NO |
|---|---|
| Gly His Arg Pro Val Xaa Xaa Xaa Xaa Xaa Xaa Xaa Xaa Xaa Xaa Xaa Xaa Xaa Xaa Xaa Xaa Xaa Xaa | 223 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa | 224 |
| Gly His Arg Val Val Xaa Xaa Xaa Xaa Xaa Xaa Xaa Xaa Xaa Xaa Xaa Xaa Xaa Xaa Xaa Xaa Xaa Xaa | 225 |
| Gly Pro Arg Val Val Xaa Xaa Xaa Xaa Xaa Xaa Xaa Xaa Xaa Xaa Xaa Xaa Xaa Xaa Xaa Xaa Xaa Xaa | 226 |
| Gly His Arg Pro Leu Xaa Xaa Xaa Xaa Xaa Xaa Xaa Xaa Xaa Xaa Xaa Xaa Xaa Xaa Xaa Xaa Xaa Xaa | 227 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa | 228 |
| Gly His Arg Val Leu Xaa Xaa Xaa Xaa Xaa Xaa Xaa Xaa Xaa Xaa Xaa Xaa Xaa Xaa Xaa Xaa Xaa Xaa | 229 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa | 230 |
| Gly His Arg Pro Val Xaa Xaa Xaa Xaa Xaa Xaa Xaa Xaa Xaa Xaa Xaa Xaa Xaa Xaa Xaa Xaa Xaa Xaa | 231 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa | 232 |
| Gly His Arg Val Val Xaa Xaa Xaa Xaa Xaa Xaa Xaa Xaa Xaa Xaa Xaa Xaa Xaa Xaa Xaa Xaa Xaa Xaa | 233 |
| Gly Pro Arg Val Val Xaa Xaa Xaa Xaa Xaa Xaa Xaa Xaa Xaa Xaa Xaa Xaa Xaa Xaa Xaa Xaa Xaa Xaa | 234 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa | 235 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa | 236 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa | 237 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa | 238 |
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa | 239 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa | 240 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa | 241 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa | 242 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa | 243 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa | 244 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa | 245 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa | 246 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
|---|---|
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 247 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 248 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 249 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 250 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 251 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 252 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 253 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 254 |
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 255 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 256 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 257 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 258 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 259 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 260 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 261 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 262 |
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 263 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 264 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 265 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 266 |
| Gly His Arg Pro Leu Xaa Xaa Xaa Xaa Xaa Xaa Xaa Xaa Xaa Xaa Xaa Xaa Xaa Xa.a Xaa Xaa Xaa Xaa Xaa Xaa Xaa Xaa Xaa | 267 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 268 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 269 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 270 |
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 271 |

TABLE 2-continued

Peptides of Formula II: Gly - His/Pro - Arg - Pro/Val - Leu/Val - Xaa$_2$ - Xaa$_{30}$

| SEQUENCE | SEQ ID NO |
|---|---|
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 272 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 273 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 274 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 275 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 276 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 277 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 278 |
| Gly His Arg Pro Val Xaa Xaa Xaa Xaa Xaa Xaa Xaa Xaa Xaa Xaa Xaa Xaa Xaa Xaa Xaa Xa.a Xaa Xaa Xaa Xaa Xaa Xaa Xaa Xaa Xaa Xaa | 279 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 280 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 281 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 282 |
| Gly His Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 283 |
| Gly Pro Arg Pro Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 284 |
| Gly His Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 285 |
| Gly Pro Arg Val Leu Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 286 |
| Gly His Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 287 |
| Gly Pro Arg Pro Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 288 |
| Gly His Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 289 |
| Gly Pro Arg Val Val Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa Xaa | 290 |

The invention claimed is:

1. A method of treating rejection of a transplanted tissue in a subject comprising administering to the subject a peptide (SEQ ID NO:294)
Gly His Arg Pro Leu Asp Lys Lys Arg Glu Glu Ala Pro Ser Leu Arg Pro Ala Pro Pro Pro Ile Ser Gly Gly Gly Tyr Arg or a salt or amide thereof, in an amount effective to treat rejection of transplanted tissue, wherein the amino terminus is

wherein R1 and R2 are either the same or different, wherein R1 and R2 are each selected from the group consisting of hydrogen and a saturated or unsaturated hydrocarbon residue, said residue having from 1 to 10 carbon atoms, and wherein the peptide, or a salt or amide thereof, comprises a peptide derived from a source selected from the group consisting of the Aalpha-chain of fibrin and the Bbeta chain of fibrin.

2. A method of inhibiting inflammation of a transplanted tissue in a subject comprising administering to the subject a peptide (SEQ ID NO:294)
Gly His Arg Pro Leu Asp Lys Lys Arg Glu Glu Ala Pro Ser Leu Arg Pro Ala Pro Pro Pro Ile Ser Gly Gly Gly Tyr Arg or a salt or amide thereof, in an amount effective to treat rejection of transplanted tissue, wherein the amino terminus is

wherein R1 and R2 are either the same or different,
wherein R1 and R2 are each selected from the group consisting of hydrogen and a saturated or unsaturated hydrocarbon residue, said residue having from 1 to 10 carbon atoms.

3. The method of claim 2, wherein the peptide, or a salt or amide thereof, comprises a peptide derived from a source selected from the group consisting of the Aalpha-chain of fibrin and the Bbeta chain of fibrin.

* * * * *